(12) United States Patent
Ritter et al.

(10) Patent No.: US 9,150,516 B2
(45) Date of Patent: Oct. 6, 2015

(54) FLUORINATION OF ORGANIC COMPOUNDS

(75) Inventors: Tobias Ritter, Cambridge, MA (US); Pingping Tang, Quincy, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 729 days.

(21) Appl. No.: 13/444,676

(22) Filed: Apr. 11, 2012

(65) Prior Publication Data

US 2012/0316341 A1    Dec. 13, 2012

Related U.S. Application Data

(60) Provisional application No. 61/474,535, filed on Apr. 12, 2011.

(51) Int. Cl.
| | |
|---|---|
| *C07D 233/10* | (2006.01) |
| *C07D 233/28* | (2006.01) |
| *C07C 67/307* | (2006.01) |
| *C07C 41/22* | (2006.01) |
| *C07C 201/12* | (2006.01) |
| *C07B 39/00* | (2006.01) |
| *C07C 209/74* | (2006.01) |
| *C07C 45/63* | (2006.01) |
| *C07C 17/16* | (2006.01) |
| *C07J 1/00* | (2006.01) |

(52) U.S. Cl.
CPC .............. *C07D 233/28* (2013.01); *C07B 39/00* (2013.01); *C07C 17/16* (2013.01); *C07C 41/22* (2013.01); *C07C 45/63* (2013.01); *C07C 67/307* (2013.01); *C07C 201/12* (2013.01); *C07C 209/74* (2013.01); *C07D 233/10* (2013.01); *C07J 1/0059* (2013.01); *C07B 2200/05* (2013.01)

(58) Field of Classification Search
CPC ........................... C07D 233/28; C07D 233/10
See application file for complete search history.

(56) References Cited

U.S. PATENT DOCUMENTS

| | | | |
|---|---|---|---|
| 3,136,774 A | 6/1964 | Stoffel | |
| 3,136,776 A | 6/1964 | Stoffel | |
| 3,137,701 A | 6/1964 | Ayer | |
| 3,641,153 A | 2/1972 | Kyburz et al. | |
| 3,972,936 A | 8/1976 | Christy | |
| 3,991,103 A | 11/1976 | Barton et al. | |
| 4,236,008 A | 11/1980 | Henderson | |
| 4,402,956 A | 9/1983 | Silvestrini et al. | |
| 4,487,773 A | 12/1984 | Temple, Jr. et al. | |
| 6,069,110 A | 5/2000 | Klaui et al. | |
| 6,127,583 A | 10/2000 | Sonoda et al. | |
| 6,160,158 A | 12/2000 | Bartlett et al. | |
| 7,108,846 B1 | 9/2006 | Marchand et al. | |
| 7,115,249 B2 | 10/2006 | Luthra et al. | |
| 8,686,158 B2 | 4/2014 | Furuya et al. | |
| 9,024,093 B2 | 5/2015 | Ritter et al. | |
| 2005/0085474 A1 | 4/2005 | Ebenbeck et al. | |
| 2005/0137421 A1 | 6/2005 | Walsh et al. | |
| 2006/0083677 A1 | 4/2006 | Brady et al. | |
| 2007/0092441 A1 | 4/2007 | Wadsworth et al. | |
| 2009/0247517 A1 | 10/2009 | Liu et al. | |
| 2011/0054175 A1 | 3/2011 | Ritter et al. | |
| 2011/0212936 A1 | 9/2011 | Furuya et al. | |
| 2011/0312903 A1 | 12/2011 | Ritter et al. | |
| 2012/0095217 A1 | 4/2012 | Ritter et al. | |
| 2012/0149900 A1 | 6/2012 | Ritter et al. | |
| 2012/0316120 A1 | 12/2012 | Ritter | |
| 2014/0018538 A1 | 1/2014 | Lee et al. | |
| 2014/0058106 A1 | 2/2014 | Ritter et al. | |

FOREIGN PATENT DOCUMENTS

| | | |
|---|---|---|
| CN | 1263882 A | 8/2000 |
| CN | 1897891 A1 | 1/2007 |
| DE | 23 60 940 A1 | 4/1975 |
| EP | 0 618 491 A1 | 10/1994 |
| EP | 0 915 094 A1 | 5/1999 |
| EP | 1 013 629 A1 | 6/2000 |
| GB | 1 177 525 A | 1/1970 |
| JP | 63-166159 A | 7/1988 |
| JP | 2001- 322984 A | 11/2001 |
| WO | WO 03/020732 A2 | 3/2003 |
| WO | WO 2005/063254 A2 | 7/2005 |
| WO | WO 2005/117872 A2 | 12/2005 |
| WO | WO 2006/078752 A2 | 7/2006 |
| WO | WO 2008/081477 A1 | 7/2008 |
| WO | WO 2008/091818 A1 | 7/2008 |
| WO | WO 2009/033751 A2 | 3/2009 |
| WO | WO 2009/100014 A1 | 8/2009 |
| WO | WO 2009/141053 A1 | 11/2009 |
| WO | WO 2009/149347 A1 | 12/2009 |
| WO | WO 2010/059943 A2 | 5/2010 |
| WO | WO 2010/081034 A2 | 7/2010 |
| WO | WO 2010/081036 A2 | 7/2010 |
| WO | WO 2011/006088 A2 | 1/2011 |
| WO | WO 2012/024604 A2 | 2/2012 |
| WO | WO 2012/054782 A2 | 4/2012 |
| WO | WO 2012/142162 A2 | 10/2012 |

OTHER PUBLICATIONS

Extended European Search Report for EP 09759505.2, mailed Jan. 20, 2012
International Search Report and Written Opinion for PCT/US2009/046401, mailed Sep. 22, 2009.
International Preliminary Report on Patentability for PCT/US2009/046401, mailed Dec. 16, 2010.
International Search Report and Written Opinion for PCT/US2009/032855, mailed Jun. 8, 2009.
International Preliminary Report on Patentability for PCT/US2009/032855, mailed Aug. 12, 2010.
Invitation to Pay Additional Fees for PCT/US2010/041561, mailed Sep. 28, 2010.
International Search Report and Written Opinion for PCT/US2010/041561, mailed Jun. 15, 2011.

(Continued)

*Primary Examiner* — Rebecca Anderson
(74) *Attorney, Agent, or Firm* — Wolf, Greenfield & Sacks, P.C.

(57) ABSTRACT

Methods for fluorinating organic compounds are described herein.

14 Claims, No Drawings

(56) References Cited

OTHER PUBLICATIONS

International Preliminary Report on Patentability for PCT/US2010/041561, mailed Jan. 19, 2012.
Extended European Search Report for EP 10729595.8, mailed May 22, 2013.
International Search Report and Written Opinion for PCT/US2010/020544, mailed Oct. 7, 2010.
International Preliminary Report on Patentability for PCT/US2010/020544, mailed Jul. 21, 2011.
Extended European Search Report for EP 09828291.6, mailed May 18, 2012.
International Search Report and Written Opinion for PCT/US2009/065339, mailed Jul. 12, 2010.
International Preliminary Report on Patentability for PCT/US2009/065339, mailed Jun. 3, 2011.
Extended European Search Report for EP 11818838.2, mailed Dec. 10, 2013.
International Search Report and Written Opinion for PCT/US2011/048451, mailed Mar. 22, 2012.
International Preliminary Report on Patentability for PCT/US2011/048451, mailed Mar. 7, 2013.
International Search Report and Written Opinion for PCT/US2012/033125, mailed Nov. 9, 2012.
International Preliminary Report on Patentability for PCT/US2012/033125, mailed Oct. 24, 2013.
Extended European Search Report for EP 10729593.3, mailed May 3, 2012.
International Search Report and Written Opinion for PCT/US2010/020540, mailed Oct. 6, 2010.
International Preliminary Report on Patentability for PCT/US2010/020540, mailed Jul. 21, 2011.
International Search Report and Written Opinion for PCT/US2011/057176, mailed May 3, 2012.
International Preliminary Report on Patentability for PCT/US2011/057176, mailed May 2, 2013.
Office Communication, mailed Feb. 25, 2013, for U.S. Appl. No. 12/996,274.
Notice of Allowance, mailed Aug. 21, 2013, for U.S. Appl. No. 12/996,274.
Notice of Allowance, mailed Dec. 4, 2013, for U.S. Appl. No. 12/996,274.
Office Communication, mailed Sep. 18, 2012, for U.S. Appl. No. 12/865,703.
Office Communication, mailed Jan. 28, 2013, for U.S. Appl. No. 12/865,703.
Office Communication, mailed Jul. 24, 2013, for U.S. Appl. No. 13/130,033.
Office Communication, mailed Dec. 19, 2013, for U.S. Appl. No. 13/130,033.
[No Author Listed] PubChem Compound Summary titled "Dadle" (Jul. 28, 2006) [Retrieved from the Internet Sep. 14, 2010: <http://pubchem.ncbi.nim.nih.gov/summary/summary.cgi?cid=6917707&loc=ec_rcs]. 4 pages.
[No Author Listed] PubChem Compound Summary titled "Enkephalin, Leucine" (Mar. 25, 2005) [Retrieved from the Internet Sep. 14, 2010: <http://pubchem.ncbi.nim.nih.gov/summary/summary.cgi?cid=3903&loc=ec_rcs 09/14/2010>]. 5 pages.
Adams et al., Nucleophilic routes to selectively fluorinated aromatics. Chem Soc Rev. 1999;28:225-31.
Ahmed et al., Boronic acids as inhibitors of steroid sulfatase. Bioorg Med Chem. Dec. 15, 2006;14(24):8564-73. Epub Sep. 14, 2006.
Alvarez-Corral et al., Silver-mediated synthesis of heterocycles. Chem Rev. Aug. 2008;108(8):3174-98. doi: 10.1021/cr0783611. Epub Jul. 17, 2008.
Andrae et al., Energy-adjustedab initio pseudopotentials for the second and third row transition elements. Theor Chem Acta. 1990;77(2):123-41.
Andrae et al., Energy-adjustedab initio pseudopotentials for the second and third row transition elements: Molecular test for M2 (M=Ag, Au) and MH (M=Ru, Os). Theor Chim Acta. 1991;78(4):247-66.
Avdeef et al., Octanol-, chloroform-, and propylene glycol dipelargonat-water partitioning of morphine-6-glucuronide and other related opiates. J Med Chem. Oct. 25, 1996;39(22):4377-81.
Balz et al., Über aromatische Fluorverbindungen, I.: Ein neues Verfahren zu ihrer Darstellung. Ber Deut Chem Ges. 1927;60:1186-90.
Becke, Density-functional thermochemistry. III. The role of exact exchange. J Chem Phys. 1993;98(7): 5648-52.
Berge et al., Pharmaceutical Salts. J. Pharmaceutical Sciences 1977;66:1-19.
Bergman et al., Fluorine-18-labeled fluorine gas for synthesis of tracer molecules. Nucl Med Biol. Oct. 1997;24(7):677-83.
Berry et al., An octahedral coordination complex of iron(VI). Science. Jun. 30, 2006;312(5782):1937-41. Epub Jun. 1, 2006.
Billingsley et al., Palladium-catalyzed borylation of aryl chlorides: scope, applications, and computational studies. Angew Chem. 2007;119(28):5455-59.
Black et al., Observations on the mechanism of halogen-bridge cleavage by unidentate ligands in square planar palladium and platinum complexes. Australian Journal of Chemistry. 1994;47(2):217227.
Bohm et al., Fluorine in medicinal chemistry. Chembiochem. May 3, 2004;5(5):637-43.
Brown et al., Transition-metal-mediated reactions for C(sp2)-F bond construction: the state of play. Angew Chem Int Ed Engl. 2009;48(46):8610-4. doi: 10.1002/anie.200902121.
Buzzi et al., The antimigraine drug, sumatriptan (GR43175), selectively blocks neurogenic plasma extravasation from blood vessels in dura mater. Br J Pharmacol. Jan. 1990;99(1):202-6.
Campbell et al., Synthesis and structure of solution-stable one-dimensional palladium wires. Nat Chem. Nov. 13, 2011;3(12):949-53. doi: 10.1038/nchem.1197.
Cámpora et al., Redox Behavior of an Organometallic Palladium(II)/Palladium(IV) System. A New Method for the Synthesis of Cationic Palladium(IV) Complexes. Organometallics. 2005;24(15):3624-3628.
Canty et al., Carbon—Oxygen Bond Formation at Metal(IV) Centers: Reactivity of Palladium(II) and Platinum(II) Complexes of the [2,6-(Dimethylaminomethyl)phenyl-N,C,N]—(Pincer) Ligand toward Iodomethane and Dibenzoyl Peroxide; Structural Studies of M(II) and M(IV) Complexes. Organometallics. 2004;23(23):5432-5439.
Canty et al., Synthesis and Characterization of Ambient Temperature Stable Organopalladium(IV) Complexes, Including Aryl-, .eta.1-Allyl-, Ethylpalladium(IV), and Pallada(IV)cyclopentane Complexes. Structures of the Poly(pyrazol-1-yl)borate Complexes PdMe3{(pz)3BH} and PdMe3{(pz)4B } and Three Polymorphs of PdMe2Et{(pz)3BH}. Organometallics. 1995;14(1):199-206.
Canty et al., Synthesis of halogeno, pseudohalogeno, and carboxylatopalladium(IV) complexes by halogen exchange. Crystal structure of azido(2,2'-bipyridyl)—benzylpalladium(II), formed on reductive elimination of ethane from Pd(N3)Me2(CH2Ph)(bpy). J Organometallic Chem. 1992;433(1-2):213-22.
Chan et al., Palladium(II)-catalyzed selective monofluorination of benzoic acids using a practical auxiliary: a weak-coordination approach. Angew Chem Int Ed Engl. Sep. 19, 2011;50(39):9081-4. doi: 10.1002/anie.201102985. Epub Jul. 11, 2011.
Chuang et al., A dinuclear palladium catalyst for a-hydroxylation of carbonyls with O2. J Am Chem Soc. Feb. 16, 2011;133(6):1760-2. doi: 10.1021/ja108396k. Epub Jan. 19, 2011.
Chung et al., Segmental spinal nerve ligation model of neuropathic pain. Methods Mol Med. 2004;99:35-45.
Constaninou et al., Xenon difluoride exchanges fluoride under mild conditions: a simple preparation of [(18)F]xenon difluoride for PET and mechanistic studies. J Am Chem Soc. Feb. 28, 2001;123(8):1780-1.
Cope et al., Electrophilic aromatic substitution reactions by platinum(II) and palladium(II) chlorides on N,N-dimethylbenzylamines J Am Chem Soc. 1968;90(4):909-913.

(56) References Cited

OTHER PUBLICATIONS

Couturier et al., Fluorinated tracers for imaging cancer with positron emission tomography. Eur J Nucl Med Mol Imaging. Aug. 2004;31(8):1182-206. Epub Jul. 6, 2004.

Czarnik, Encoding methods for combinatorial chemistry. Curr Opin Chem Biol. Jun. 1997;1(1):60-6.

Danielson et al., Use of 19F NMR to probe protein structure and conformational changes. Annu Rev Biophys Biomol Struct. 1996;25:163-95.

Dick et al., A highly selective catalytic method for the oxidative functionalization of C—H bonds. J Am Chem Soc. Mar. 3, 2004;126(8):2300-1.

Dick et al., Carbon—Nitrogen Bond-Forming Reactions of Palladacycles with Hypervalent Iodine Reagents. Organometallics. 2007;26(6):1365-1370.

Dick et al., Unusually stable palladium(IV) complexes: detailed mechanistic investigation of C—O bond-forming reductive elimination. J Am Chem Soc. Sep. 21, 2005;127(37):12790-1.

Edwards et al., In vitro and in vivo studies of neutral cyclometallated complexes against murine leukemias. Canadian Journal of Chemistry. 2005;83(6-7):980-989.

Ehlers et al., A set of f-polarization functions for pseudo-potential basis sets of the transition metals Sc Cu, Y Ag and La Au. Chem Phys Lett. 1993;208(1-2):111-14.

Ernst et al., Presynaptic dopaminergic deficits in Lesch-Nyhan disease. N Engl J Med. Jun. 13, 1996;334(24):1568-72.

Espinet et al., (CN)-chelate, N,N'-bridged dimeric palladium complexes derived from hydrazones PhC(R):NN'HPh. X-ray structure of [Pd(o-C6H4C(R):NNPh)L]2 [R = Me, L = P(OMe)3]. Inorg Chem., 1989;28(23):4207-4211.

Evans, The determination of the paramagnetic susceptibility of substances in solution by nuclear magnetic resonance. J Chem Soc. 1959;2003-2005.

Fier et al., Copper-mediated fluorination of aryl iodides. J Am Chem Soc. Jul. 4, 2012;134(26):10795-8. doi: 10.1021/ja304410x. Epub Jun. 22, 2012.

Fier et al., Copper-mediated fluorination of arylboronate esters. Identification of a copper(III) fluoride complex. J Am Chem Soc. Feb. 20, 2013;135(7):2552-9. doi: 10.1021/ja310909q. Epub Feb. 5, 2013.

Folgado et al., Fluxionality in hexacoordinated copper(II) complexes with 2,2':6',2"-terpyridine (terpy) and related ligands: structural and spectroscopic investigations. Inorg Chem. 1990;29(11):2035-2042.

Ford et al., Regioselectivity in metallation reactions of 2-(2'-naphthyl)pyridine: l'-versus 3'-reactivity in mercuration and palladation reactions. Crystal structure of chloro(pyridine) [2-(2—pyridiny)naphthyl-C3,N]palladium. J Organometallic Chem. 1995;493(1-2):215-20.

Fraser et al., Molecular Fluoro Palladium Complexes. J Am Chem Soc. 1997;119(20):4769-70.

Fulmer et al., NMR Chemical Shifts of Trace Impurities: Common Laboratory Solvents, Organics, and Gases in Deuterated Solvents Relevant to the Organometallic Chemist. Organometallics. 2010;29(9):2176-2179.

Furuya et al., Carbon-Fluorine Bond Formation for the Synthesis of Aryl Fluorides. Synthesis. 2010;11:1804-1821.

Furuya et al., Carbon-fluorine bond formation. Curr Opin Drug Discov Devel. Nov. 2008;11(6):803-19.

Furuya et al., Carbon-fluorine reductive elimination from a high-valent palladium fluoride. J Am Chem Soc. Aug. 6, 2008;130(31):10060-1. doi: 10.1021/ja803187x. Epub Jul. 11, 2008.

Furuya et al., Catalysis for fluorination and trifluoromethylation. Nature. May 26, 2011;473(7348):470-7. doi: 10.1038/nature10108.

Furuya et al., Fluorination of boronic acids mediated by silver(I) triflate. Org Lett. Jul. 2, 2009;11(13):2860-3. doi: 10.1021/ol901113t.

Furuya et al., Mechanism of C—F reductive elimination from palladium(IV) fluorides. J Am Chem Soc. Mar. 24, 2010;132(11):3793-807. doi: 10.1021/ja909371t.

Furuya et al., Palladium-mediated fluorination of arylboronic acids. Angew Chem Int Ed Engl. 2008;47(32):5993-6. doi: 10.1002/anie.200802164.

Furuya et al., Silver-mediated fluorination of functionalized aryl stannanes. J Am Chem Soc. Feb. 11, 2009;131(5):1662-3. doi: 10.1021/ja8086664.

Gay et al., Lithiations of .alpha.- and .beta.-(dimethylaminomethyl)naphthalenes with n-butyllithium and condensations with benzophenone. Some related results. J Am Chem Soc. 1967;89(10):2297-2303.

Gilicinski et al., On the relative power of electrophilic fluorinating reagents of the N F class. J Fluor Chem. 1992;59(1):157-162.

Grushin et al., Ar—F Reductive Elimination from Palladium(II) Revisited. Organometallics. 2007;26(20):4997-5002.

Grushin et al., Facile Ar-CF3 bond formation at Pd. Strikingly different outcomes of reductive elimination from [(Ph3P)2Pd(CF3)Ph] and [(Xantphos)Pd(CF3)Ph]. J Am Chem Soc. Oct. 4, 2006;128(39):12644-5.

Grushin et al., Is fluoride bonded to two Pd acceptors still basic? Three CH2C12 molecules encapsulating a Pd2(mu-F)2 square and new implications for catalysis. Angew Chem Int Ed Engl. Dec. 2, 2002;41(23):4476-9.

Grushin et al., Palladium Fluoride Complexes: One More Step toward Metal-Mediated C—F Bond Formation. Chemistry—A European Journal. 2002;8(5):1006-14.

Gullick et al., Catalytic asymmetric heterogeneous aziridination of styrene using Cu2+-exchanged zeolite Y: effect of the counter-cation on enantioselectivity and on the reaction profile. New J Chem. 2004;28:1470-1478.

Hariharan et al., The influence of polarization functions on molecular orbital hydrogenation energies. Theor Chim Acta. 1973;28(3):213-22.

Hartwell et al., The formation of palladium(II)— and platinum(II)— carbon bonds by proton abstraction from benzo[h]quinoline and 8-methylquinoline. J Chem Soc D. 1970:912.

Harvey et al., A new general synthesis of polycyclic aromatic compounds based on enamine chemistry. J Org Chem. 1991;56(3):1210-1217.

Henriksen et al., Recent development and potential use of μ- and κ-opioid receptor ligands in positron emission tomography studies. Drug Dev Res. 2006;67(12):890-904.

Henriksen et al., Syntheses, biological evaluation, and molecular modeling of 18F-labeled 4-anilidopiperidines as mu-opioid receptor imaging agents. J Med Chem. Dec. 1, 2005;48(24):7720-32.

Huang et al., Silver-mediated trifluoromethoxylation of aryl stannanes and arylboronic acids. J Am Chem Soc. Aug. 31, 2011;133(34):13308-10. doi: 10.1021/ja204861a. Epub Aug. 9, 2011.

Hull et al., Palladium-catalyzed fluorination of carbon-hydrogen bonds. J Am Chem Soc. Jun. 7, 2006;128(22):7134-5.

Ishiyama et al., Mild iridium-catalyzed borylation of arenes. High turnover numbers, room temperature reactions, and isolation of a potential intermediate. J Am Chem Soc. Jan. 23, 2002;124(3):390-1.

Jasim et al., Contrasting Reactivity of Fluoropyridines at Palladium and Platinum: C—F Oxidative Addition at Palladium, P—C and C—F Activation at Platinum. Organometallics 2004;23(26):6140-49.

Jeschke, The Unique Role of Fluorine in the Design of Active Ingredients for Modern Crop Protection. ChemBioChem. 2004;5(5):570-589.

Jones et al., Systemic gabapentin and S(+)-3-isobutyl-gamma-aminobutyric acid block secondary hyperalgesia. Brain Res. Nov. 9, 1998;810(1-2):93-9.

Julia et al., Orientation de la palladation du noyau naphtalenique dans les α et β dimethylaminomethyl naphtalenes. J Organometallic Chem. 1975;102(2):239-43.

Jun et al., The effect of intrathecal gabapentin and 3-isobutyl gamma-aminobutyric acid on the hyperalgesia observed after thermal injury in the rat. Anesth Analg. Feb. 1998;86(2):348-54.

Jung et al., Organic Chemistry on Solid Supports. Angew Chem Int Ed Engl. 1996;35(1):17-42.

(56) References Cited

OTHER PUBLICATIONS

Kamlet et al., Application of palladium-mediated (18)F-fluorination to PET radiotracer development: overcoming hurdles to translation. PLoS One. 2013;8(3):e59187. doi: 10.1371/journal.pone.0059187. Epub Mar. 12, 2013.
Kaspi et al., Xenon difluoride induced aryl iodide reductive elimination: a simple access to difluoropalladium(II) complexes. Inorg Chem. Jan. 7, 2008;47(1):5-7. Epub Dec. 4, 2007.
Khusnutdinova et al., The aerobic oxidation of a Pd(II) dimethyl complex leads to selective ethane elimination from a Pd(III) intermediate. J Am Chem Soc. Feb. 1, 2012;134(4):2414-22. doi: 10.1021/ja210841f. Epub Jan. 20, 2012.
Kilbourn et al., Fluorine-18 labeling of proteins. J Nucl Med. Apr. 1987;28(4):462-70.
Kim et al., An experimental model for peripheral neuropathy produced by segmental spinal nerve ligation in the rat. Pain. Sep. 1992;50(3):355-63.
Kirk, Fluorination in Medicinal Chemistry: Methods, Strategies, and Recent Developments. Org Process Res Dev. 2008;12(2):305-321.
Laali et al., N-(trifluoromethylsulfonyl)aryloxytrifluoromethylsulfoximines [ArO—So(CF3)=NTf] and N-aryltriflimides Ar—N(Tf)2 by thermal and photolytic dediazoniation of [ArN2] [BF4] in [BMIM] [Tf2N] ionic liquid: exploiting the ambident nucleophilic character of a "nonnucleophilic" anion. J Org Chem. Aug. 31, 2007;72(18):6758-62. Epub Aug. 1, 2007.
Lanci et al., Oxidatively induced reductive elimination from ((t)Bu2bpy)Pd(Me)2: palladium(IV) intermediates in a one-electron oxidation reaction. J Am Chem Soc. Nov. 4, 2009;131(43):15618-20. doi: 10.1021/ja905816q.
Lasne et al., Chemistry of beta(+)-emitting compounds based on fluorine-18. In: Contrast Agents II. 2002;222:201-58.
Lee et al., a fluoride-derived electrophilic late-stage fluorination reagent for PET imaging. Science. Nov. 4, 2011;334(6056):639-42. doi: 10.1126/science.1212625.
Lee et al., Nickel-mediated oxidative fluorination for PET with aqueous [18F] fluoride. J Am Chem Soc. Oct. 24, 2012;134(42):17456-8. doi: 10.1021/ja3084797. Epub Oct. 12, 2012.
Li et al., Synthesis and local anesthetic activity of fluoro-substituted imipramine and its analogues. Bioorg Med Chem Lett. Jul. 1, 2007;17(13):3733-5. Epub Apr. 10, 2007.
Liang et al., Introduction of fluorine and fluorine-containing functional groups. Angew Chem Int Ed Engl. Aug. 5, 2013;52(32):8214-64. doi: 10.1002/anie.201206566. Epub Jul. 19, 2013.
Liu et al., Oxidative aliphatic C—H fluorination with fluoride ion catalyzed by a manganese porphyrin. Science. Sep. 14, 2012;337(6100):1322-5. doi: 10.1126/science.1222327.
Liu et al., Synthesis and properties of 12-fluororetinal and 12-fluororhodopsin. Model system for fluorine-19 NMR studies of visual pigments. J Am Chem Soc. 1981;103(24):7195-201.
Lockner et al., Practical Radical Cyclizations with Arylboronic Acids and Trifluoroborates. Org. Lett. 2011;13(20):5628-5631.
Lovey et al., Fluorinated retinoic acids and their analogs. 3. Synthesis and biological activity of aromatic 6-fluoro analogs. J Med Chem. 1982;25(1):71-75.
Mack et al., Effect of Chelate Ring Expansion on Jahn—Teller Distortion and Jahn—Teller Dynamics in Copper(II) Complexes. Inorg Chem. 2012;51(14):7851-7858.
Maeda et al., Amino Acids and Peptides. X. : Leu-Enkephalin Analogues Containing a Fluorinated Aromatic Amino Acid. Chem Pharm Bull. 1989;37(3):826-28.
Maimone et al., Evidence for in situ catalyst modification during the Pd-catalyzed conversion of aryl triflates to aryl fluorides. J Am Chem Soc. Nov. 16, 2011;133(45):18106-9. doi: 10.1021/ja208461k. Epub Oct. 21, 2011.
Makleit et al., Synthesis and chemical transformation of halogen-containing morphine derivatives. Magyar Kemikusok Lapja. 1997;52(6):282-89.

Marshall et al., Single-Crystal X-ray and Solution 13C NMR Study of Fluoro(pnitrophenyebis(triphenylphosphine)palladium(II). Are There Effects of Through-Conjugation? Organometallics. 1998;17(24):5427-30.
Matthews et al., Equilibrium acidities of carbon acids. VI. Establishment of an absolute scale of acidities in dimethyl sulfoxide solution. J Am Chem Soc. 1975;97(24):7006-7014.
Mazzotti et al., Palladium(III)-Catalyzed Fluorination of Arylboronic Acid Derivatives. J Am Chem Soc. Sep. 25, 2013;135(38):14012-5. doi: 10.1021/ja405919z. Epub Sep. 16, 2013.
McGaraughty et al., Effects of A-317491, a novel and selective P2X3/P2X2/3 receptor antagonist, on neuropathic, inflammatory and chemogenic nociception following intrathecal and intraplantar administration. Br J Pharmacol. Dec. 2003;140(8):1381-8. Epub Nov. 17, 2003.
McMurtrey et al., Pd-catalyzed C—H fluorination with nucleophilic fluoride. Pd-catalyzed C—H fluorination with nucleophilic fluoride. Org Lett. Aug. 17, 2012;14(16):4094-7. doi: 10.1021/01301739f. Epub Jul. 30, 2012.
Mendoza-Espinosa et al., Synthesis of 4- and 4,5-Functionalized Imidazol-2-ylidenes from a Single 4,5-Unsubstituted Imidazol-2-ylidene. J Am Chem Soc. 2010;132(21):7264-7265.
Miao et al., PET of EGFR Expression with an $^{18}$F-Labeled Affibody Molecule. J Nucl Med. 2012;53:1110-1118 (10.2967/jnumed.111.100842).
Miller et al., Synthesis of 11C, 18F, 15O, and 13N radiolabels for positron emission tomography. Angew Chem Int Ed Engl. 2008;47(47):8998-9033. doi: 10.1002/anie.200800222.
Mirica et al., Structure and electronic properties of Pd(III) complexes. Coord Chem Rev. 2013;257(2):299-314.
Muller et al., Fluorine in pharmaceuticals: looking beyond intuition. Science. Sep. 28, 2007;317(5846):1881-6.
Muller et al., The rhodium(II)-catalyzed aziridination of olefins with { [(4-nitrophenyl)sulfonyfl]imino}phenyl-lambda3-iodane. Canadian J of Chem. 1998;76(6):738-750.
Murphy et al., One-pot synthesis of arylboronic acids and aryl trifluoroborates by Ir-catalyzed borylation of arenes. Org Lett. Mar. 1, 2007;9(5):757-60. Epub Feb. 3, 2007.
Murphy et al., Organometallic Fluorides: Compounds Containing Carbonminus signMetalminus signFluorine Fragments of d-Block Metals. Chem Rev. Dec. 18, 1997;97(8):3425-3468.
Nagakura et al., Allodynia and hyperalgesia in adjuvant-induced arthritic rats: time course of progression and efficacy of analgesics. J Pharmacol Exp Ther. Aug. 2003;306(2):490-7. Epub May 1, 2003.
Nesterenko et al., Quantum-Chemical Study of the Mechanism and Regioselectivity of Transannular Cyclization of Dienes of the Bicyclo[3.3.1]nonane Series Treated with Bromosuccinimide and F-TEDA-BF. Theor Exp Chem. 2002;38:156-61.
Niedenzu et al., Boron-nitrogen compounds. 99. Studies on B-(pyrazol-1-yl)pyrazaboles. Inorg Chem. 1984;23(23):3713-3716.
Noel et al., Accelerating palladium-catalyzed C—F bond formation: use of a microflow packed-bed reactor. Angew Chem Int Ed Engl. Sep. 12, 2011;50(38):8900-3. doi: 10.1002/anie.201104652. Epub Aug. 11, 2011.
Nozaki-Taguchi et al., A novel model of primary and secondary hyperalgesia after mild thermal injury in the rat. Neurosci Lett. Sep. 18, 1998;254(1):25-8.
Nyffeler et al., Selectfluor: Mechanistic Insight and Applications. Angew Chem Int Ed Engl. 2004;44(2):192-212.
Onishi et al., Palladium Polypyrazolylborate Complexes Containing a Pd—C Bond. Chem Lett. 1976:955-58.
Ortiz et al., A Convenient Synthesis of Methyl- and Isopropyl-Benzyl Ethers Using Silver(II) Oxide as Reagent. Synth Commun. 1993;23(6):749-56.
Pangborn et al., Safe and Convenient Procedure for Solvent Purification. Organometallics. 1996;15(5):1518-1520.
Park et al., Metabolism of fluorine-containing drugs. Annu Rev Pharmacol Toxicol. 2001;41:443-70.
Pawlikowski et al., Alkyl carbon-nitrogen reductive elimination from platinum(IV)-sulfonamide complexes. J Am Chem Soc. Aug. 29, 2007;129(34):10382-93. Epub Aug. 2, 2007.

(56) References Cited

OTHER PUBLICATIONS

Perdew et al., Accurate and simple analytic representation of the electron-gas correlation energy. Phys Rev B Condens Matter. Jun. 15, 1992;45(23):13244-13249.
Pérez et al., Thermal Study of [Pd(2-Phpy)C3(L)] Complexes (L=pyridines and amines). Journal of Thermal Analysis and Calorimetry. 2001;66(2):361-370.
Phelps, Positron emission tomography provides molecular imaging of biological processes. Proc Natl Acad Sci U S A. Aug. 1, 2000;97(16):9226-33.
Powers et al., Bimetallic palladium catalysis: direct observation of Pd(III)—Pd(III) intermediates. J Am Chem Soc. Dec. 2, 2009;131(47):17050-1. doi: 10.1021/ja906935c.
Powers et al., Bimetallic Pd(III) complexes in palladium-catalysed carbon—heteroatom bond formation. Nat Chem. Jul. 2009;1(4):302-9.
Powers et al., Bimetallic redox synergy in oxidative palladium catalysis. Acc Chem Res. Jun. 19, 2012;45(6):840-50. doi: 10.1021/ar2001974. Epub Oct. 27, 2011.
Powers et al., Bimetallic reductive elimination from dinuclear Pd(III) complexes. J Am Chem Soc. Oct. 13, 2012;132(40):14092-103. doi: 10.1021/ja1036644.
Powers et al., Connecting binuclear Pd(IV) and mononuclear Pd(IV) chemistry by Pd—Pd bond cleavage. J Am Chem Soc. Jul. 25, 2012;134(29):12002-9. doi: 10.1021/ja304401u. Epub Jul. 17, 2012.
Powers et al., On the mechanism of palladium-catalyzed aromatic C—H oxidation. J Am Chem Soc. Oct. 20, 2010;132(41):14530-6. doi: 10.1021/ja1054274.
Powers et al., Palladium(III) in Synthesis and Catalysis. Top Organomet Chem. Jan. 1, 2011;503:129-156.
Privalov et al., Theoretical Studies of the Mechanism of Aerobic Alcohol Oxidation with Palladium Catalyst Systems. Organometallics.2005;24(5):885-893.
Purser et al., Fluorine in medicinal chemistry. Chem Soc Rev. Feb. 2008;37(2):320-30. doi: 10.1039/b610213c. Epub Dec. 13, 2007.
Rebstock et al., Synthesis and deprotonation of 2-(pyridyl)phenols and 2-(pyridyl)anilines. Org Biomol Chem. Sep. 7, 2003;1(17):3064-8.
Reed et al., Intermolecular interactions from a natural bond orbital, donor-acceptor viewpoint. Chem Rev. 1988;88(6):899-926.
Roe et al., Structure and Solution Dynamics of [(Ph3P)2Pd(Ph)(Fhf)]. Organometallics. 2000;19(22):4575-82.
Ryabov et al., Synthesis by ligand exchange, structural characterization, and aqueous chemistry of ortho-palladated oximes. Inorg Chem. 1992;31(14):3083-3090.
Sandford, Elemental fluorine in organic chemistry (1997-2006). J Fluorine Chem. 2007;128:90-104.
Sasaki et al., Solid phase synthesis and opioid receptor binding activities of [D-Ala2, D-Leu5]enkephalin analogs containing a fluorinated aromatic amino acid. Chem Pharm Bull (Tokyo). Nov. 1990;38(11):3162-3.
Serguchev et al., Transannular additions of selectfluor and xenon difluoride: regioselectivity and mechanism. J Phys Org Chem. 2011;24(5):407-13.
Sheldrick, A short history of SHELX. Acta Cryst Sect A. 2008;A64:112-122.
Singh et al., Recent highlights in electrophilic fluorination with 1-chloromethyl-4-fluoro- 1,4-diazoniabicyclo[2.2.2]octane bis(tetrafluoroborate). Acc Chem Res. Jan. 2004;37(1):31-44.
Sladojevich et al., Late-stage deoxyfluorination of alcohols with PhenoFluor. J Am Chem Soc. Feb. 20, 2013;135(7):2470-3. doi: 10.1021/ja3125405. Epub Feb. 11, 2013.
Still et al., Rapid chromatographic technique for preparative separations with moderate resolution. J Org Chem. 1978;43(14):2923-2925.
Strassman et al., Sensitization of meningeal sensory neurons and the origin of headaches. Nature. Dec. 12, 1996;384(6609):560-4.
Sun et al., Room-temperature nucleophilic aromatic fluorination: experimental and theoretical studies. Angew Chem Int Ed Engl. Apr. 21, 2006;45(17):2720-5.
Szostak et al., Electron transfer reduction of carboxylic acids using SmI2—H20—Et3N. Org Lett. Feb. 3, 2012;14(3):840-3. doi: 10.1021/ol203361k. Epub Jan. 24, 2012.
Tang et al., Deoxyfluorination of phenols. J Am Chem Soc. Aug. 3, 2011;133(30):11482-4. doi: 10.1021/ja2048072. Epub Jul. 12, 2011.
Tang et al., Silver-catalyzed late-stage fluorination. J Am Chem Soc. Sep. 1, 2010;132(34):12150-4. doi: 10.1021/ja105834t.
Tang et al., Silver-mediated fluorination of aryl silanes. Tetrahedron. Jun. 17, 2011;67(24):4449-4454.
Taylor et al., Catalytic asymmetric heterogeneous aziridination of styrene using CuHY: effect of nitrene donor on enantioselectivity. J Chem Soc Perkin Trans 2. 2001:1714-1723.
Teare et al., Synthesis and reactivity of [18F]N-fluorobenzenesulfonimide. Chem Commun (Camb). Jun. 21, 2007;2007(23):2330-2.
Thordarson, Determining association constants from titration experiments in supramolecular chemistry. Chem Soc Rev. Mar. 2011;40(3):1305-23. doi: 10.1039/c0cs00062k. Epub Dec. 1, 2010.
Ting et al., Arylfluoroborates and alkylfluorosilicates as potential PET imaging agents: high-yielding aqueous biomolecular 18F-labeling. J Am Chem Soc. Sep. 28, 2005;127(38):13094-5.
Tius et al., The reaction of XeF2 with trialkylvinylstannanes: Scope and some mechanistic observations. Tetrahedron. 1995;51(14):3997-4010.
Tredwell et al., Electrophilic fluorination of organosilanes. Org Biomol Chem. Jan. 7, 2006;4(1):26-32. Epub Nov 23, 2005.
Trofimenko, Boron-pyrazole chemistry. II. Poly(1-pyrazolyl)-borates. J Am Chem Soc. 1967;89(13):3170-3177.
Trofimenko, Polypyrazolylborates, a new class of ligands. Acc Chem Res. 1971;4(1):17-22.
Trofimenko, Recent advances in poly(pyrazolyl)borate (scorpionate) chemistry. Chem Rev. 1993;93(3):943-980.
Valenzano et al., Pharmacological and pharmacokinetic characterization of the cannabinoid receptor 2 agonist, GW405833, utilizing rodent models of acute and chronic pain, anxiety, ataxia and catalepsy. Neuropharmacology. Apr. 2005;48(5):658-72.
Vasdev et al., On the preparation of fluorine-18 labelled XeF(2) and chemical exchange between fluoride ion and XeF(2). J Am Chem Soc. Oct. 30, 2002;124(43):12863-8.
Vincente et al., Synthesis of Tris- and Tetrakis(pyrazol-l-Aborate Gold(III) Complexes. Crystal Structures of [Au {κ2-N,N'-BH(Pz)3 } C12] (pz = Pyrazol-1-yl) and [Au {κ2-N,N'-B(Pz)4 } (κ2-C,N-C6H4CH2NMe2-2)]C1O4• CHC13. Inorg Chem. 2002;41(7):1870-1875.
Walker et al., The VR1 antagonist capsazepine reverses mechanical hyperalgesia in models of inflammatory and neuropathic pain. J Pharmacol Exp Ther. Jan. 2003;304(1):56-62.
Wang et al., Versatile Pd(OTf)2 x 2 H2O-catalyzed ortho-fluorination using NMP as a promoter. J Am Chem Soc. Jun. 10, 2009;131(22):7520-1. doi: 10.1021/ja901352k.
Watson et al., Formation of ArF from LPdAr(F): catalytic conversion of aryl triflates to aryl fluorides. Science. Sep. 25, 2009;325(5948):1661-4. doi: 10.1126/science.1178239. Epub Aug. 13, 2009.
Weiss et al., Electrostatic Activation of Hypervalent Organo-Iodine Compounds: Bis(onio)-Substituted Aryliodine(III) Salts. Angew Chem Int Ed. 1994;33(8):891-93.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Norte Dame, IN. 1972:268-98.
Woo et al., Direct conversion of pyranose anomeric OH—>F—>R in the artemisinin family of antimalarial trioxanes. Tetrahedron Lett. 1998;39(12):1533-36.
Xanthos et al., Animal Models of Chronic Pain: Chronic post-ischemia pain: a novel animal model of Complex Regional Pain Syndrome Type I produced by prolonged hindpaw ischemia and reperfusion in the rat. J Pain. 2004;5:S1. Abstract B01.
Yahav et al., Synthesis of the Elusive (R3P)2MF2 (M = Pd, Pt) Complexes. J Am Chem Soc. 2003;125(45):13634-35.

(56) References Cited

OTHER PUBLICATIONS

Yahav-Levi et al., Competitive aryl-iodide vs aryl-aryl reductive elimination reactions in Pt(IV) complexes: experimental and theoretical studies. J Am Chem Soc. Jan. 16, 2008;130(2):724-31.
Yaksh et al., An automated flinch detecting system for use in the formalin nociceptive bioassay. J Appl Physiol (1985). Jun. 2001;90(6):2386-402.
Yamada et al., Synthesis and Reaction of New Type I—N Ylide, N-Tosyliminoiodinane. Chem Lett. 1975;4(4):361-62.
Yandulov et al., Aryl-fluoride reductive elimination from Pd(II): feasibility assessment from theory and experiment. J Am Chem Soc. Feb. 7, 2007;129(5):1342-58.
Ye et al., Mild copper-mediated fluorination of aryl stannanes and aryl trifluoroborates. J Am Chem Soc. Mar. 27, 2013;135(12):4648-51. doi: 10.1021/ja400300g. Epub Mar. 13, 2013.
Zhang et al., Interception of the radicals produced in electrophilic fluorination with radical traps (Tempo, Dmpo) studied by electrospray ionization mass spectrometry. Rapid Commun Mass Spectrom. 2006;20(12):1877-82.
Zhang et al., Investigation of radical cation in electrophilic fluorination by ESI-MS. Org Lett. Sep. 1, 2005;7(18):3877-80.
Invitation to Pay Additional Fees for PCT/US2013/061968, mailed Jan. 3, 2014.
International Search Report and Written Opinion for PCT/US2013/061968, mailed Mar. 7, 2014.
Casitas et al., Nucleophilic aryl fluorination and aryl halide exchange mediated by a Cu(I)/Cu(III) catalytic cycle. *J Am Chem Soc*. Dec. 7, 2011;133(48):19386-92. doi: 10.1021/ja2058567. Epub Nov. 14, 2011.
Lin et al., Interactions of aziridines with nickel complexes: oxidative-addition and reductive-elimination reactions that break and make C—N. bonds. *J Am Chem Soc*. Mar. 27, 2002;124(12):2890-1.
Extended European Search Report for EP 12771755.1, mailed Aug. 5, 2014.
Invitation to Pay Additional Fees for PCT/US2014/061066, mailed Jan. 12, 2015.
International Preliminary Report on Patentability for PCT/US2013/061968, mailed Apr. 9, 2015.
PubMed Compounds NCBI. Accession No. CID 525788. Oct. 7, 2005.
Brazier et al., The condensation of alpha-Keto-beta-anilino-alphabeta-diphenyl ethane and its Homologues with phenylcarbimide and with phenylthiocarbimide. J Chem Soc. 1912;101:2352-58.
Fujimoto et al., PhenoFluor: Practical Synthesis, New Formulation, and Deoxyfluorination of Heteroaromatics. Org Process Res Dev. Aug. 15, 2014;18(8):1041-1044. Epub Jul. 23, 2014.
Hayashi et al., 2,2-Difluoro-1,3-dimethylimidazolidine (DFI). A new fluorinating agent. Chem Commun (Camb). Aug. 7, 2002;(15):1618-9. Chem Commun (Camb). Aug. 7, 2002;(15):1618-9.
Holschumacher et al., Sulfur and Selenium Activation by Frustrated NHC/B(C6F5)3 Lewis Pairs; Conformational Flexibility of Products. Z Naturforsch. 2011;66b:371-77.
Maas et al., Dication ethers. 7. Dication ether salts from cyclic bisureas. J Heterocyclic Chemistry. 1985;22(3):907-10.
Maas et al., Dication disulfides by reaction of thioureas and related compounds with trifluoromethanesulfonic anhydride. The role of triflic anhydride as an oxidizing agent. J Org Chem. 1981;46(8):1606-1610.
Mccombie et al., The condensation of a-Keto-beta-anilino-alpha-phenylethane and its Homologues with Carbonyl Chloride, Phenylcarbimide, and Phenylthiocarbimide. J Chem Soc. 1913;103:56-63.
Pidlypnyi et al., N-Heterocyclic carbenes from ylides of indolyl-imidazolium, azaindolyl-imidazolium, and indolyl-triazolium salts, and their borane adducts. Tetrahedron. 2014;70(45):8672-80.
Williams et al., Main group metal halide complexes with sterically hindered thioureas. VIII. Complexes of lead(II) halides with 1,3-dimethyl-2(3H)-imidazolethione. Inorganica Chimica Acta. 1988;144(2):237-40.

FLUORINATION OF ORGANIC COMPOUNDS

RELATED APPLICATIONS

The present application claims priority under 35 U.S.C. §119(e) to U.S. provisional application: U.S. Ser. No. 61/474,535, filed Apr. 12, 2011 which is incorporated herein by reference in its entirety.

GOVERNMENT RIGHTS

This invention was made with government support under GM088237 awarded by National Institutes of Health. The government has certain rights in the invention.

FIELD OF THE INVENTION

The invention relates to compounds, composition and methods of fluorinating an organic compound using a fluorinating agent.

BACKGROUND OF INVENTION

Functionalized aryl fluorides are used as pharmaceuticals and agrochemicals, in part due to their favorable pharmacological properties such as increased metabolic stability (see, for example, Müller et al., *Science* 2007, 317, 1881-1886; Kirk et al., *Org. Process Res. Dev.* 2001, 41, 443-470; and Jeschke, P. *ChemBioChem* 2004, 5, 570-589). Aryl fluorides also find applications as tracers in positron emission tomography using the [$^{18}$F] isotope (Lasne, et al. In *Contrast Agents II*, 2002; Vol. 222, pp 201-258). Fluorine has the highest electronegativity, the highest oxidation potential, and the smallest anionic radius of all elements, each of which complicates carbon-fluorine bond formation when compared to other carbon-heteroatom bond formations (see, for example, Chambers, R. D., *Fluorine in organic chemistry*. Oxford: New York, 2004; and Furuya et al. *Curr. Opin. Drug Discov. Devel.* 2008, 11, 803-819).

SUMMARY OF INVENTION

Described herein are novel compounds, compositions and methods for fluorinating organic compounds.

In one aspect, the present invention is directed to a compound of formula (I):

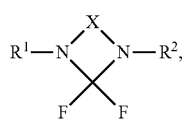

(I)

wherein
$R^1$ and $R^2$ are each independently selected from $C_{1-6}$ alkyl, $C_{6-12}$ aryl, $C_{6-12}$ aralkyl, 6-12 membered heteroaryl, 6-12 membered heteroaralkyl, 6-12 membered heterocyclyl and 6-12 membered heterocyclylalkyl, each of which is substituted with 0-3 occurrences of $R^5$;
X is an optionally substituted $C_2$-$C_5$ alkenylene moiety; and
each $R^5$ is independently selected from halo, $C_{1-8}$ alkyl, $C_{1-8}$ haloalkyl, $C_{1-8}$ alkoxy, $C_{6-12}$ aryl and 6-12 membered heteroaryl.

In some embodiments, $R^1$ and $R^2$ are each independently selected from $C_{6-12}$ aryl, $C_{6-12}$ aralkyl, 6-12 membered heteroaryl, 6-12 membered heteroaralkyl, 6-12 membered heterocyclyl and 6-12 membered heterocyclylalkyl, each of which is substituted with 0-3 occurrences of $R^5$. In some embodiments, $R^1$ and $R^2$ are each independently selected from $C_{6-12}$ aryl, 6-12 membered heteroaryl and 6-12 membered heterocyclyl. In some embodiments, $R^1$ and $R^2$ are each independently selected from $C_{6-12}$ membered aryl or 6-12 membered heteroaryl. In some embodiments, $R^1$ and $R^2$ are $C_{6-12}$ membered aryl (e.g., phenyl) substituted with 0-3 occurrences of $R^5$. In some embodiments, $R^1$ and $R^2$ are $C_{6-12}$ membered aryl (e.g., phenyl) substituted with 2 occurrences of $R^5$. In some embodiments, $R^1$ and $R^2$ are phenyl substituted with 0-3 occurrences of $R^5$. In some embodiments, $R^1$ and $R^2$ are phenyl substituted with 2 occurrences of $R^5$.

In some embodiments, X is a optionally substituted $C_2$ alkenylene. In some embodiments, the alkeneylene moiety has a single double bond In some embodiments, the compound of formula (I) is a compound of formula (Ia):

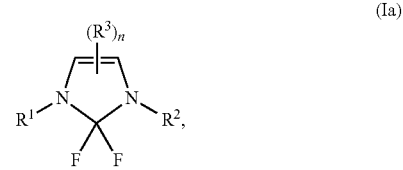

(Ia)

wherein $R^1$ and $R^2$ are as described herein;
each $R^3$ is independently selected from $C_{1-8}$ alkyl, nitro, cyano, halo, $C_{1-8}$ haloalkyl, $C_{1-8}$ alkoxy, $C_{6-12}$ aryl, $C_{6-12}$ aralkyl, 6-12 membered heteroaryl, 6-12 membered heterocyclyl and 6-12 membered heterocyclylalkyl; and
n is 0, 1 or 2.

In some embodiments, n is 0. In some embodiments, n is 1. In some embodiments, n is 2.

In some embodiments, each $R^3$ is independently selected from halo, $C_{1-8}$ alkyl, $C_{1-8}$ haloalkyl or $C_{1-8}$ alkoxy. In some embodiments, each $R^3$ is $C_{1-8}$ haloalkyl (e.g., trifluoromethyl). In some embodiments, each $R^3$ is halo (e.g., fluoro or chloro).

In some embodiments, the compound of formula (I) is a compound of formula (Ib):

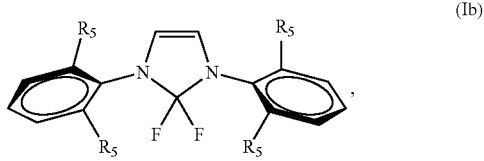

(Ib)

wherein each $R^5$ is as described herein. In some embodiments, each $R^5$ is independently selected from $C_{1-8}$ alkyl, $C_{1-8}$ haloalkyl and $C_{1-8}$ alkoxy. In some embodiments, each $R^5$ is $C_{1-8}$ alkyl (e.g., isopropyl).

In some embodiments, the compound of formula (I) is a compound of formula (Ic)

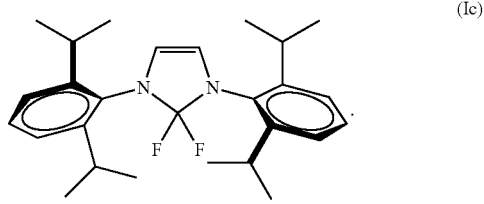

(Ic)

In another aspect, the present invention is directed to a method of fluorinating a hydroxy organic compound or a tautomer thereof, the method comprising mixing a compound of formula (I) and the organic compound under conditions sufficient to fluorinate the substrate, thereby providing a fluorinated organic compound.

In some embodiments, the fluorinated organic compound comprises $^{18}F$ or $^{19}F$.

In some embodiments, the hydroxy organic compound comprises an aryl group (e.g., phenol). In some embodiments, the hydroxy organic compound comprises a hydroxy heteroaryl group. In some embodiment, the hydroxy organic compound comprises a vinyl alcohol. In some embodiments, the hydroxy organic compound comprises an aryl group (e.g., phenol) and the fluorinated organic compound is a fluorinated phenyl group.

In some embodiments, the hydroxy organic compound comprises a tautomer. In some embodiments, the hydroxy organic compound comprises a tautomer of a hydroxy heterocyclyl group (e.g., a pyridone).

In some embodiments, the method further comprises a reagent. In some embodiments, the reagent is a zinc reagent (e.g., diphenyl zinc).

In some embodiments, the reagent is present in a catalytic amount (e.g., 5 mol %, 10 mol %, 20 mol %, 30 mol %, 50 mol % or 75 mol %).

In some embodiments, the hydroxy organic compound or tautomer thereof is a precursor or a pharmaceutically acceptable compound.

In some embodiments, the method further comprises an additional fluorine source. In some embodiments, the fluorine source is $F^-$ or a precursor thereof. In some embodiments, the fluorine source is a salt. In some embodiments, the fluorine source is a cesium salt (e.g., CsF). In some embodiments, the fluorine source is a potassium salt (e.g., KF).

In some embodiments, the method further comprises a solvent. In some embodiments, the solvent is a nonpolar solvent. In some embodiments, the solvent is toluene. In some embodiments, the solvent is dioxane. In some embodiments, the solvent is benzene.

In some embodiments, the method further comprises an inert atmosphere.

In some embodiments, the reaction is performed under anhydrous conditions.

In some embodiments, the reaction proceeds at ambient temperature.

In some embodiments, the reaction comprises cooling.

In some embodiments, the reaction comprises a source of energy.

In some embodiments, the reaction comprises heat.

In some embodiments, the fluorinated organic compound comprises an aryl group. In some embodiments, the fluorinated organic compound is a pharmaceutically acceptable compound or a prodrug thereof.

In some embodiments, a compound employed in the method (e.g., a compound of formula (I) or a hydroxy organic compound or tautomer thereof) is immobilized on a solid support.

In some embodiments, the fluorination takes place at a late stage in the synthesis of the fluorinated organic compound. In some embodiments, the fluorination is the last step in the synthesis of the fluorinated organic compound. In some embodiments, the organic compound is made using a multi step synthesis.

In some embodiments, the method further comprises purification of the fluorinated organic compound from the reaction mixture.

In some embodiments, the yield of the fluorinated organic compound from the organic compound is at least about 20% (e.g., at least about 30%, 40%, 50%, 60%, 70%, 75%, 80%, 85%, 90%, 95% or 98%).

In another aspect, the present invention is directed to a method of producing a compound of formula (I), the method comprising reacting a compound of formula (II):

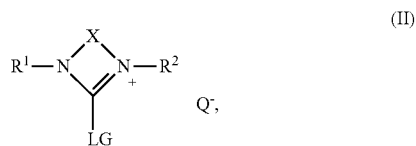

wherein $R^1$, $R^2$, $R^3$, $R^4$, $R^5$ and X are as described herein; wherein
LG is a leaving group; and
Q is an anion;
with a fluorine source to produce the compound of formula (I).

In some embodiments, LG is a halogen (e.g., chloro or bromo). In some embodiments, LG is a triflate group.

In some embodiments, Q is a halogen anion (e.g., Cl$^-$). In some embodiments, Q is a triflate anion.

In some embodiments, $R^1$ and $R^2$ are each independently selected from $C_{6-12}$ aryl, $C_{6-12}$ aralkyl, 6-12 membered heteroaryl, 6-12 membered heteroaralkyl, 6-12 membered heterocyclyl and 6-12 membered heterocyclylalkyl, each of which is substituted with 0-3 occurrences of $R^5$. In some embodiments, $R^1$ and $R^2$ are each independently selected from $C_{6-12}$ aryl, 6-12 membered heteroaryl and 6-12 membered heterocyclyl. In some embodiments, $R^1$ and $R^2$ are each independently selected from $C_{6-12}$ membered aryl or 6-12 membered heteroaryl. In some embodiments, $R^1$ and $R^2$ are $C_{6-12}$ membered aryl (e.g., phenyl) substituted with 0-3 occurrences of $R^5$. In some embodiments, $R^1$ and $R^2$ are $C_{6-12}$ membered aryl (e.g., phenyl) substituted with 2 occurrences of $R^5$. In some embodiments, $R^1$ and $R^2$ are phenyl substituted with 0-3 occurrences of $R^5$. In some embodiments, $R^1$ and $R^2$ are phenyl substituted with 2 occurrences of $R^5$.

In some embodiments, X is an optionally substituted $C_2$ alkenylene. In some embodiments, the alkeneylene moiety has a single double bond In some embodiments, the compound of formula (II) is a compound of formula (IIa):

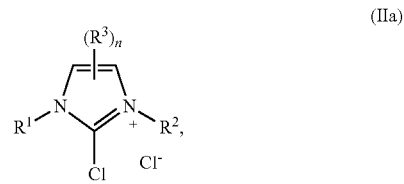

wherein $R^1$ and $R^2$ are as described herein;
each $R^3$ is independently selected from $C_{1-8}$ alkyl, nitro, cyano, halo, $C_{1-8}$ haloalkyl, $C_{1-8}$ alkoxy, $C_{6-12}$ aryl, $C_{6-12}$ aralkyl, 6-12 membered heteroaryl, 6-12 membered heterocyclyl and 6-12 membered heterocyclylalkyl; and
n is 0, 1 or 2.

In some embodiments, n is 0. In some embodiments, n is 1. In some embodiments, n is 2.

In some embodiments, each $R^3$ is independently selected from halo, $C_{1-8}$ alkyl, $C_{1-8}$ haloalkyl or $C_{1-8}$ alkoxy. In some embodiments, each $R^3$ is $C_{1-8}$ haloalkyl (e.g., trifluoromethyl). In some embodiments, each $R^3$ is halo (e.g., fluoro or chloro).

In some embodiments, the compound of formula (II) is a compound of formula (IIb):

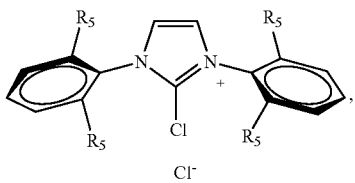

(IIb)

wherein each $R^5$ is as described herein. In some embodiments, each $R^5$ is independently selected from $C_{1-8}$ alkyl, $C_{1-8}$ haloalkyl and $C_{1-8}$ alkoxy. In some embodiments, each $R^5$ is $C_{1-8}$ alkyl (e.g., isopropyl).

In some embodiments, the compound is a compound of formula (IIc),

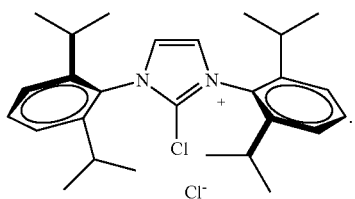

(IIc)

In some embodiments, the method further comprises reacting the compound of formula (I) with a hydroxy organic compound or a tautomer thereof under conditions sufficient to fluorinate the organic compound, thereby providing a fluorinated organic compound.

In some embodiments, the fluorinated organic compound comprises $^{18}F$ or $^{19}F$.

In some embodiments, the hydroxy organic compound comprises an aryl group (e.g., phenol). In some embodiments, the hydroxy organic compound comprises a hydroxy heteroaryl group. In some embodiment, the hydroxy organic compound comprises a vinyl alcohol. In some embodiments, the hydroxy organic compound comprises an aryl group (e.g., phenol) and the fluorinated organic compound is a fluorinated phenyl group.

In some embodiments, the hydroxy organic compound comprises a tautomer. In some embodiments, the hydroxy organic compound comprises a tautomer of a hydroxy heterocyclyl group (e.g., a pyridone).

In some embodiments, the hydroxy organic compound or tautomer thereof is a precursor to a pharmaceutically acceptable compound.

In some embodiments, the method further comprises a reagent. In some embodiments, the reagent is a zinc reagent (e.g., diphenyl zinc).

In some embodiments, the reagent is present in a catalytic amount (e.g., 5 mol %, 10 mol %, 20 mol %, 30 mol %, 50 mol % or 75 mol %).

In some embodiments, the method further comprises a fluorine source. In some embodiments, the fluorine source is F or a precursor thereof. In some embodiments, the fluorine source is a salt. In some embodiments, the fluorine source is a cesium salt (e.g., CsF). In some embodiments, the fluorine source is a potassium salt (e.g., KF).

In some embodiments, the method further comprises a solvent. In some embodiments, the solvent is a nonpolar solvent. In some embodiments, the solvent is toluene.

In some embodiments, the solvent is dioxane. In some embodiments, the solvent is benzene.

In some embodiments, the method further comprises an inert atmosphere.

In some embodiments, the reaction is performed under anhydrous conditions.

In some embodiments, the reaction proceeds at ambient temperature.

In some embodiments, the reaction comprises cooling.

In some embodiments, the reaction comprises a source of energy.

In some embodiments, the reaction comprises heat.

In some embodiments, the fluorinated organic compound comprises an aryl group. In some embodiments, the fluorinated organic compound is a pharmaceutically acceptable compound or a prodrug thereof.

In some embodiments, a compound employed in the method (e.g., a compound of formula (I) or a hydroxy organic compound or tautomer) is immobilized on a solid support.

In some embodiments, the fluorination takes place at a late stage in the synthesis of the fluorinated organic compound. In some embodiments, the fluorination is the last step in the synthesis of the fluorinated organic compound. In some embodiments, the organic compound is made using a multi step synthesis.

In some embodiments, the method further comprises purification of the fluorinated organic compound from the reaction mixture.

In some embodiments, the yield of the fluorinated organic compound from the organic compound is at least about 20% (e.g., at least about 30%, 40%, 50%, 60%, 70%, 75%, 80%, 85%, 90%, 95% or 98%).

In another aspect, the present invention is directed to a reaction mixture comprising a compound of formula (II) and a fluorine source.

In some embodiments, the reaction mixture further comprises a reagent. In some embodiments, the reagent is a zinc reagent (e.g., diphenyl zinc).

In another aspect, the present invention is directed to a composition comprising a compound of formula (II) and a fluorine source.

In some embodiments, the composition further comprises a reagent. In some embodiments, the reagent is a zinc reagent (e.g., diphenyl zinc).

In another aspect, the present invention is directed to a reaction mixture comprising a compound of formula (I) or (II), a hydroxy organic compound or a tautomer thereof and a fluorine source.

In some embodiments, the organic compound comprises an aryl group (e.g., phenyl). In some embodiments, the organic compound comprises a phenol group.

In some embodiments, the reaction mixture further comprises a fluorine source. In some embodiments, the fluorine source is F or a precursor thereof. In some embodiments, the fluorine source is a salt. In some embodiments, the fluorine source is a cesium salt (e.g., CsF). In some embodiments, the fluorine source is a potassium salt (e.g., KF).

In some embodiments, the reaction mixture further comprises a solvent. In some embodiments, the solvent is a nonpolar solvent. In some embodiments, the solvent is toluene. In some embodiments, the solvent is dioxane. In some embodiments, the solvent is benzene.

In some embodiments, the solvent is a nonpolar solvent. In some embodiments, the solvent is toluene.

In some embodiments, the reaction mixture further comprises a reagent. In some embodiments, the reagent is a zinc reagent (e.g., diphenyl zinc).

In another aspect, the present invention is directed to a composition comprising a compound of formula (I) and an additional component. In some embodiments, the component is a substrate. In some embodiments, the substrate is an organic compound comprising an aryl group.

In some embodiments, the composition further comprises a reagent. In some embodiments, the reagent is a zinc reagent (e.g., diphenyl zinc).

In some embodiments, the component is a reagent. In some embodiments, the reagent is a fluoride source (e.g., cesium fluoride or potassium fluoride).

In some embodiments, the composition comprises a plurality of reagents.

In some embodiments, the component is a solvent. In some embodiments, the solvent is a non-polar solvent. In some embodiments, the solvent is toluene. In some embodiments, the solvent is dioxane. In some embodiments, the solvent is benzene.

In another aspect, the present invention is directed to a compound of formula (II):

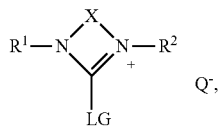

(II)

wherein
$R^1$ and $R^2$ are each independently selected from $C_{1-6}$ alkyl, $C_{6-12}$ aryl, $C_{6-12}$ aralkyl, 6-12 membered heteroaryl, 6-12 membered heteroaralkyl, 6-12 membered heterocyclyl and 6-12 membered heterocyclylalkyl, each of which is substituted with 0-3 occurrences of $R^5$;
X is an optionally substituted $C_2$-$C_5$ alkenylene moiety;
each $R^5$ is independently selected from halo, $C_{1-8}$ alkyl, $C_{1-8}$ haloalkyl, $C_{1-8}$ alkoxy, $C_{6-12}$ aryl and 6-12 membered heteroaryl,
LG is a leaving group; and
Q is an anion.

In some embodiments, Q is not a chloride anion. In some embodiments, LG is not a chloro group. In some embodiments, Q is not a chloride anion and LG is not a chloro group.

In some embodiments, Q is a triflate anion. In some embodiments, LG is a triflate group.

In some embodiments, Q is a triflate anion and LG is a triflate group.

In some embodiments, the compound is a compound of formula (IId):

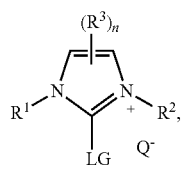

(IId)

wherein $R^3$ and n are as described herein.

In some embodiments, the compound is a compound of formula (IIe):

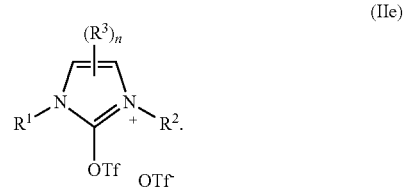

(IIe)

In another aspect, the present invention is directed to a kit comprising a compound of formula (I) and a container.

In some embodiments, the container is a vial. In some embodiments, the container is a sealed ampule. In some embodiments, the container contains an inert gas.

In some embodiments, the kit further comprises instructions for use of the compound of formula (I).

In some embodiments, the kit further comprises a reagent. In some embodiments, the kit further comprises a substrate. In some embodiments, the substrate is an organic compound comprising an aryl group.

DEFINITIONS

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. The term "alkylene" refers to a divalent alkyl, e.g., —CH$_2$—, —CH$_2$CH$_2$—, and —CH$_2$CH$_2$CH$_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent. The term "alkenylene" refers to a divalent alkenyl, e.g., —CH$_2$=CH$_2$—, and —CH$_2$=CH$_2$CH$_2$—.

The terms "alkylamino" and "dialkylamino" refer to —NH(alkyl) and —NH(alkyl)$_2$ radicals respectively. The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to an aromatic monocyclic, bicyclic, or tricyclic hydrocarbon ring system, wherein any ring atom capable of substitution can be substituted (e.g., by one or more substituents). Examples of aryl moieties include, but are not limited to, phenyl, naphthyl, and anthracenyl. An aryl moiety may also be a "heteroaryl" moiety. Heteroaryl refers to an aromatic monocyclic, bicyclic, or tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Any ring atom can be substituted (e.g., by one or more substituents). The heterocyclyl groups can contain fused rings. Fused rings are rings that share a common carbon atom. Examples of heterocyclyl include, but are not limited to, tetrahydrofuranyl, tetrahydropyranyl, piperidinyl, morpholino, pyrrolinyl, pyrimidinyl, quinolinyl, and pyrrolidinyl.

The term "cycloalkenyl" refers to partially unsaturated, nonaromatic, cyclic, bicyclic, tricyclic, or polycyclic hydrocarbon groups having 5 to 12 carbons, preferably 5 to 8 carbons. The unsaturated carbon may optionally be the point of attachment of the cycloalkenyl substituent. Any ring atom can be substituted (e.g., by one or more substituents). The cycloalkenyl groups can contain fused rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The unsaturated carbon or the heteroatom may optionally be the point of attachment of the heterocycloalkenyl substituent. Any ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-10 carbon atoms. In some embodiments, aliphatic groups contain 1-8 carbon atoms, 1-7 carbon atoms, 1-6 carbon atoms, 1-5 carbon atoms, 1-4 carbon atoms, 1-3 carbon atoms, or 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "labeled", as used herein, means the replacement of a fluorine atom on an organic compound with a $F^{18}$ or $F^{19}$ fluorine isotope wherein the isotope is present on the organic compound in an amount greater than 1.5, 2, 5, 10, 50, 100 or 1000 times greater than that found in nature.

The term "unsaturated", as used herein, means that a moiety has one or more double or triple bonds.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Any atom can be substituted. Suitable substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkylamino, dialkylamino, $SO_3H$, sulfate, phosphate, methylenedioxy (—O—$CH_2$—O— wherein oxygens are attached to vicinal atoms), ethylenedioxy, oxo, thioxo (e.g., C=S), imino(alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The details of one or more embodiments of the invention are set forth in the accompanying drawings and the description below. Other features, objects, and advantages of the invention will be apparent from the description and drawings, and from the claims.

All references cited herein, whether in print, electronic, computer readable storage media or other form, are expressly incorporated by reference in their entirety, including but not limited to, abstracts, articles, journals, publications, texts, treatises, internet web sites, databases, patents, patent applications and patent publications.

DETAILED DESCRIPTION

Described herein are methods of fluorinating reagents and methods of making fluorinated organic compounds. Upon making a fluorinating reagent (which may be isolated or used in situ) a reaction of a hydroxy organic compound or tautomer thereof and a fluorinating agent is described herein. This subsequent reaction provides a fluorinated organic compound in which the hydroxyl group (or tautomeric carbonyl) of the organic compound is replaced with a fluorine substituent (for example, see Scheme 1).

Scheme 1.

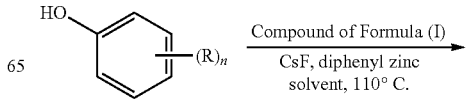

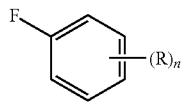

Scheme 2.

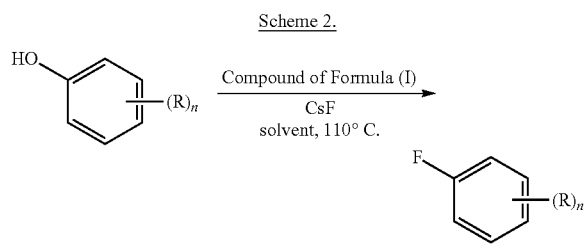

While the above schemes depict hydroxy phenyl compounds, the reaction is not limited to phenyl and may contain a number of other chemical groups. In Scheme 1, R is a substituent and n may be 0, 1, 2, 3, 4 or 5. Exemplary substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkylamino, dialkylamino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). The substituents are independently any one single, or any subset of the aforementioned substituents. A substituent may itself be substituted with any one of the above substituents. In some embodiments, two R groups may be taken together to form a ring, e.g., an aryl, heteroaryl, cyclyl or heterocyclyl ring, which may itself be further substituted with any one of the above substituents.

Organic Compounds

Compounds (e.g., a compound of formula (I) or (II)) useful in a method of fluorinating a hydroxy organic compound of tautomer thereof are described herein. The organic compound may be a small organic molecule or a large organic molecule. A small organic molecule includes any molecule having a molecular weight of less than 1000 g/mol, of less than 900 g/mol, of less than 800 g/mol, of less than 700 g/mol, of less than 600 g/mol, of less than 500 g/mol, of less than 400 g/mol, of less than 300 g/mol, of less than 200 g/mol or of less than 100 g/mol. A large organic molecule include any molecule of between 1000 g/mol to 5000 g/mol, of between 1000 g/mol to 4000 g/mol, of between 1000 g/mol to 3000 g/mol, of between 1000 g/mol to 2000 g/mol, or of between 1000 g/mol to 1500 g/mol. Organic compounds include aryl, heteroaryl and heterocyclyl containing compounds.

In some embodiments, the organic compound contains a chiral center. In some embodiments, the organic compound is further substituted with one or more functional groups (e.g., alcohols, aldehydes, ketones, esters, alkenes, alkoxy groups, cyano groups, amines, amides and N-oxides). In some embodiments, the functional groups are unprotected. In some embodiments, the organic compound is a precursor of a pharmaceutically acceptable compound.

Fluorine Sources

The methods described herein generally include a fluorine source. In some embodiments, the fluorine source is a nucleophilic fluorine source. In some embodiments, the fluorine source is commercially available. In some embodiments, the fluorine source is also an inorganic fluorine source. Exemplary fluorine sources include cesium fluoride (CsF) and potassium fluoride (KF).

The fluorine source may be enriched with a particular isotope of fluorine. In some embodiments, the fluorine source is labeled with $^{19}F$ (i.e., provides a $^{19}F$ fluorine to the reaction mixture). In some embodiments, reaction of the $^{19}F$-labeled fluorine source with a compound within the reaction mixture ultimately provides a fluorinated $^{19}F$-labeled organic compound.

In some embodiments, the fluorine source is labeled with $^{18}F$ (i.e., provides a $^{18}F$ fluorine to the reaction mixture). In some embodiments, reaction of the $^{18}F$-labeled fluorine source with a compound in the reaction mixture provides a fluorinated $^{18}F$-labeled organic compound.

However, in some embodiments, the fluorine source is labeled with a mixture of $^{18}F$ and $^{19}F$. In some embodiments, reaction of the mixture of $^{19}F$ and $^{18}F$ fluorine source with a compound in the reaction mixture provides a mixture of fluorinated $^{19}F$-labeled organic compound and fluorinated $^{18}F$-labeled organic compound.

Reaction Conditions

Described herein are methods of producing a fluorinating reagent and methods of fluorinating hydroxy organic compounds (e.g., a phenol) or tautomers thereof (e.g., pyridine) using a fluorinating agent (e.g., a compound of formula (I)). In some embodiments, the reaction further comprises a solvent. Exemplary solvents include non-polar solvents (e.g., toluene, dioxane or benzene). In some embodiments, the reaction is performed under ambient temperature, pressure and atmosphere. In some embodiments, the reaction is performed in an inert atmosphere (e.g., an atmosphere that is substantially free of dioxygen or water). In some embodiments, the reaction is performed under anhydrous conditions (e.g., in a solvent that is substantially free of water). In some embodiments, the reaction is heated. In some embodiments, the reaction is cooled. In some embodiments, the reaction is performed at room temperature (e.g., about 20-25° C.).

In some embodiments, the reaction proceeds in a single step. In a one-step procedure, an organic compound comprising a substrate and a fluorine source, and optionally an additional reagent such as a base (e.g., NaOH, KOH, BaO, MgO, $NaHCO_3$, $KHCO_3$, $Na_2CO_3$, $Ba(OH)_2$ or 2,6-lutidine) or a salt (e.g., cesium fluoride), to yield a fluorinated organic compound. In some embodiments, the additional reagent is a zinc reagent (e.g., diphenyl zinc). In some embodiments, the reaction proceeds in two steps. In a two-step procedure, the organic compound comprising substrate may be first reacted with a compound described herein in the presence of an optional additional reagent, such as a base (e.g., NaOH, KOH, BaO, MgO, $NaHCO_3$, $KHCO_3$, $Na_2CO_3$, $Ba(OH)_2$ or 2,6-lutidine). In some embodiments, an intermediate product is isolated from the first reaction. An intermediate product may be further reacted with a fluorinating agent in the second step. In some embodiments, each step further comprises a solvent, and the solvents may be the same or may be different. For example, the first step may take place in acetonitrile, while the second step may take place in acetone. In some embodiments, each step may be performed at a different temperature. For example, the first step may further comprise cooling (e.g., to 0° C.), while the second step may proceed at ambient temperature.

In some embodiments, a compound of the present invention or a compound of the methods described herein is immobilized on a solid support. The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, polyacrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998)), and include those useful in techniques such as the "split and pool" or "parallel" synthesis techniques, solid-phase and solution-phase techniques, and encoding techniques (see, for example, Czarnik, A. W., *Curr. Opin. Chem. Bio*., (1997) 1, 60).

In some embodiments, the fluorination takes place at a late stage in the synthesis of the fluorinated organic compound. In some embodiments, the fluorination is the last step in the synthesis of the fluorinated organic compound.

In some embodiments, subsequent to the reaction, one or more components of the reaction mixture (e.g., a fluorinated organic compound) are purified from the reaction mixture. In some embodiments, the fluorinated organic compound is purified by column chromatography on silica gel. In some embodiments, the fluorinated organic compound is purified by preparative thin-layer chromatography.

Reaction Products

Described herein are methods of making fluorinated organic compounds. In some embodiments, the fluorinated organic compounds are generated from their corresponding precursors in yields of at least about 60% (e.g., at least about 65%, 70%, 75%, 80%, 85%, 90% or 95%).

The reaction conditions described herein are tolerant of many functional groups as well as chiral centers. In some embodiments, the fluorinated organic compound is further substituted by one or more functional groups, such as aldehydes, ketones, esters, alkenes, alkoxy groups, cyano groups, amines, amides and N-oxides. In some embodiments, the fluorinated organic compound contains a chiral center that is derived from the starting material. The stereochemistry at the chiral center may remain substantially unchanged (e.g., little to no racemization or epimerization of the chiral center occurs during the reaction). In some embodiments, the fluorinated organic compound comprises $^{19}$F. In some embodiments, the $^{19}$F-containing fluorinated organic compound is an imaging agent, such as an MRI imaging agents. In some embodiments, the $^{19}$F-containing fluorinated organic compound may be used as a probe, such as a biological NMR probes for use in in vivo NMR spectroscopy.

In some embodiments, the fluorinated organic compound comprises $^{18}$F. In some embodiments, the $^{18}$F-containing fluorinated organic compound is an imaging agent, such as a PET imaging agent.

In some embodiments, the fluorinated organic compound is a compound having pharmaceutical activity. Exemplary fluorinated organic compounds include (13S)-3-fluoro-13-methyl-7,8,9,11,12,13,15,16-octahydro-6H-cyclopenta[a]phenanthren-17(14H)-one, (R)-(6-fluoroquinolin-4-yl)((2S, 4S,8R)-8-vinylquinuclidin-2-yl)methyl acetate or fluoroestrone.

Kits

The compounds used in the methods described herein (e.g., a hydroxy organic compound or tautomer thereof and a fluorinating agent) may be provided in a kit. The kit includes (a) a compound used in a method described herein (e.g., a compound of formulas (I) and (II)), and, optionally (b) informational material. The informational material can be descriptive, instructional, marketing or other material that relates to the methods described herein and/or the use of the compounds for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to methods for using the compound.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In some embodiments, the components of the kit are stored under inert conditions (e.g., under Nitrogen or another inert gas such as Argon). In some embodiments, the components of the kit are stored under anhydrous conditions (e.g., with a desiccant). In some embodiments, the components are stored in a light blocking container such as an amber vial.

A compound described herein can be provided in any form, e.g., liquid, dried or lyophilized form. It is preferred that a compound described herein be substantially pure and/or sterile. When a compound described herein is provided as a dried form, reconstitution generally is by the addition of a suitable solvent.

The kit can include one or more containers for the composition containing a compound described herein. In some embodiments, the kit contains separate containers, dividers or compartments for the composition and informational material. For example, the composition can be contained in a bottle, vial, or ampule, and the informational material can be contained in a plastic sleeve or packet. In other embodiments, the separate elements of the kit are contained within a single, undivided container. For example, the composition is contained in a bottle, vial or ampule that has attached thereto the informational material in the form of a label. In some embodiments, the kit includes a plurality (e.g., a pack) of individual containers, each containing one or more unit dosage forms (e.g., a dosage form described herein) of a compound described herein. The containers of the kits can be air tight, waterproof (e.g., impermeable to changes in moisture or evaporation), and/or light-tight.

EXAMPLES

Materials and Methods

Solvents other than methanol were dried by passage through alumina. Except as indicated otherwise, reactions were magnetically stirred and monitored by thin layer chromatography (TLC) using EMD TLC plates pre-coated with 250 μm thickness silica gel 60 F254 plates and visualized by fluorescence quenching under UV light. In addition, TLC plates were stained using ceric ammonium molybdate or potassium permanganate stain. Flash chromatography was performed on Dynamic Adsorbents Silica Gel 40-63 μm particle size or Whatman Silica Gel 60 μm particle size using a forced flow of eluent at 0.3-0.5 bar pressure. Concentration under reduced pressure was performed by rotary evaporation at 25-30° C. at appropriate pressure. Purified compounds were further dried under high vacuum (0.01-0.05 Torr). NMR spectra were recorded on a Varian Mercury 400 (400 MHz for $^1$H, 100 MHz for $^{13}$C, 375 MHz for $^{19}$F, and 126 MHz for $^{31}$P acquisitions), Unity/Inova 500 (500 MHz for $^1$H, 125 MHz for $^{13}$C acquisitions), or Unity/Inova 600 (600 MHz for $^1$H acquisitions) spectrometer. $^{13}$C NMR spectra are recorded $^1$H decoupled. $^{19}$F NMR spectra are recorded $^1$H coupled. Chemical shifts are reported in ppm with the solvent resonance as the internal standard. Data is reported as follows: s=singlet, d=doublet, t=triplet, q=quartet, h=heptet, m=multiplet, br=broad; coupling constants in Hz; integration. High-resolution mass spectra were obtained on Jeol AX-505 or SX-102 spectrometers at the Harvard University Mass Spectrometry Facilities. Sodium hydroxide was purchased from Mallinckrodt chemicals, Molecular sieves 3 Å were purchased from EMD chemicals and finely grinded and dried at 130° C. overnight prior to use. NMR spectroscopic data of known compounds correspond to the data given in the appropriate references. Pyridine and triethylamine were distilled over calcium hydride. NMR spectroscopic data of known compounds correspond to the data given in the appropriate references.

Example 1

Preparation of Fluorinating Reagents

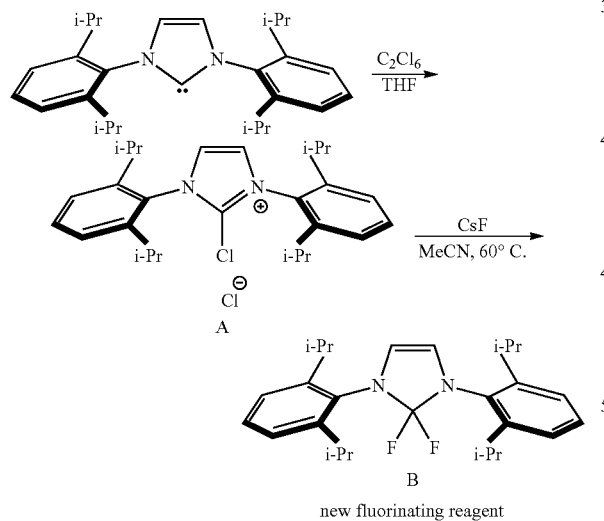

N,N'-1,3-bis(2,6-diisopropylphenyl)-2,2-dicholoimidazolidene (A)

To N,N'-1,3-bis(2,6-diisopropylphenyl)imidazol-2-ylidene (11.6 g, 30.0 mmol, 1.00 equiv) in 200 mL of THF at −40° C. was added 1,1,1,2,2,2-hexachloroethane (8.38 mg, 36.0 mmol, 1.20 equiv). The reaction mixture was warmed to 23° C. and was stirred for 24 h. The reaction mixture was cooled to −40° C. and filtered off and filter cake was washed with cold THF to afford 11.7 g of compound A as a colorless solid (85%).

NMR Spectroscopy: $^1$H NMR (500 MHz, CD$_3$CN, 23° C., δ): 8.51 (s, 2H), 7.75 (t, J=7.8 Hz, 2H), 7.56 (d, J=7.8 Hz, 4H), 2.37 (m, 4H), 1.31 (d, J=6.8 Hz, 12H), 1.25 (d, J=6.8 Hz, 12H). $^{13}$C NMR (500 MHz, CD$_3$CN, 23° C., δ): 146.4, 133.8, 129.5, 127.8, 126.3, 118.3, 30.2, 24.3, 23.5.

(See e.g., Mendoza-Espinosa et al., J. Am. Chem. Soc., 132:7264-7265 (2010)).

N,N'-1,3-bis(2,6-diisopropylphenyl)-2,2-difluoroimidazolidene (B)

To N,N'-1,3-bis(2,6-diisopropylphenyl)-2,2-dicholoimidazolidene (1.20 g, 2.60 mmol, 1.00 equiv) in 20 mL of MeCN at 23° C. was added CsF (1.58 g, 10.4 mmol, 4.00 equiv). The reaction mixture was stirred for 24 h at 60° C. The reaction mixture was cooled to 23° C. and concentrated under reduced pressure. To the residue was added toluene and the mixture was filtered through a pad of Celite eluting with toluene. The filtrate is concentrated under reduced pressure to afford 960 mg of compound B as a colorless solid (87%).

NMR Spectroscopy: $^1$H NMR (500 MHz, CD$_3$Cl, 23° C., δ): 7.39 (t, J=7.8 Hz, 2H), 7.20 (d, J=7.8 Hz, 4H), 5.88 (s, 2H), 3.35 (m, 4H), 1.25 (d, J=6.8 Hz, 12H), 1.20 (d, J=6.8 Hz, 12H). $^{13}$C NMR (500 MHz, CD$_3$Cl, 23° C., δ): 150.8, 131.1, 129.5, 125.8, 124.1, 112.5, 28.6, 25.6, 23.9. $^{19}$F NMR (375 MHz, CDCl$_3$, 23° C., δ): −36.5 ppm.

Example 2

X-Ray Structure of the Intermediate in the Fluorination Reaction

To 4-methoxyphenol (5.07 mg, 0.0408 mmol, 1.00 equiv) in benzene (1.0 mL) at 23° C. was added N,N'-1,3-bis(2,6-diisopropylphenyl)-2,2-difluoroimidazolidene (B) (20.9 mg, 0.0490 mmol, 1.20 equiv). The reaction mixture was stirred at 23° C. for 10 min in a sealed vial. The benzene was evaporated. The residue was washed with ether and then redissolved in CH$_2$Cl$_2$ (1.0 mL). The intermediate I was recrystallized from a layered mixture of CH$_2$Cl$_2$ and ether to afford colorless crystals.

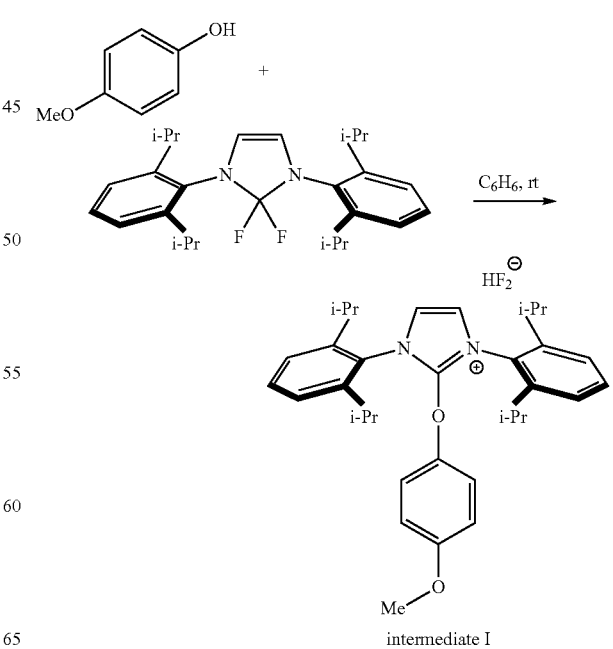

intermediate I

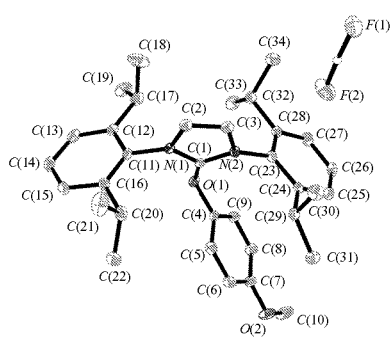

X-Ray Structure of Intermediate I

Example 3

Evaluation of Fluorination Reaction with Other Fluorination Reagents and General Procedure for Fluorination Reaction

To 4-methoxyphenol (2.5 mg, 0.020 mmol, 1.0 equiv) in toluene (0.20 mL) at 23° C. was added CsF (9.1 mg, 0.060 mmol, 3.0 equiv), and fluorination reagent (0.0240 mmol, 1.20 equiv). The reaction mixture was stirred at 110° C. for 20 h in a sealed vial, then cooled to 23° C. To the reaction mixture was added 3-nitrofluorobenzene (2.00 μL, 0.0188 mmol). The yield was determined by comparing the integration of the $^{19}$F NMR (375 MHz, 23° C.) resonance of 3-nitrofluorobenzene (−112.0 ppm). Yields are reported in Table 1.

TABLE 1

Fluorinating Reagent Evaluation

| Fluorination reagents: | MeCN | dioxane | toluene |
| --- | --- | --- | --- |
| [IPr-CF2 imidazolinium difluoride] | 0% | 88% | 82% |
| [1,3-dimethyl imidazolidinium difluoride] | 0% | 0% | 0% |
| [Et2N=SF2]+ BF4− | 0% | 0% | 0% |
| [morpholino-N=SF2]+ BF4− | 0% | 0% | 0% |

TABLE 1-continued

Fluorinating Reagent Evaluation

| Fluorination reagents: | MeCN | dioxane | toluene |
| --- | --- | --- | --- |
| Et2N-SF3 (DAST) | 0% | 0% | 0% |
| (MeOCH2CH2)2N-SF3 (Deoxo-Fluor) | 0% | 0% | 0% |

TABLE 2

Fluorination of Compounds

[R-C6H4-OH + IPr·CF2 (1.2 eq), CsF (3.0 eq), toluene → R-C6H4-F]

4-fluoronitrobenzene: 96%[a] (3 h, 80° C.)

methyl 4-fluorobenzoate: >99%[a] (3 h, 80° C.)

TABLE 2-continued
Fluorination of Compounds
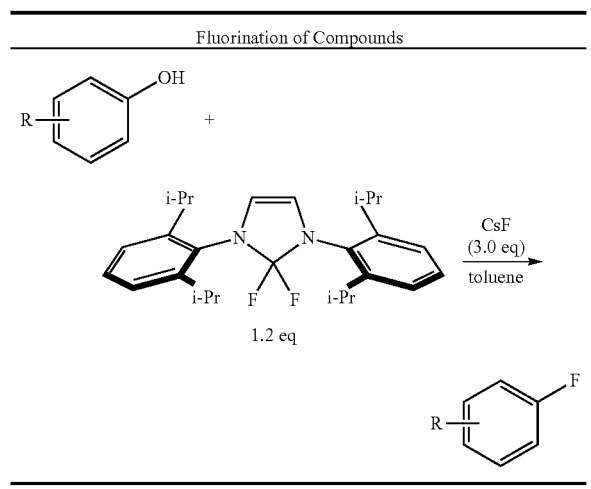
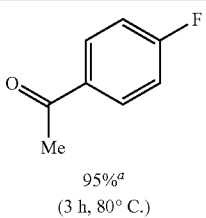
95%[a]
(3 h, 80° C.)
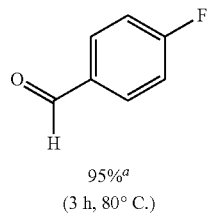
95%[a]
(3 h, 80° C.)
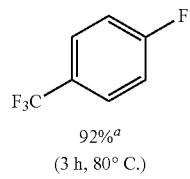 [SMILES: Fc1ccc(C(F)(F)F)cc1]
92%[a]
(3 h, 80° C.)
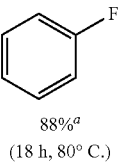
88%[a]
(18 h, 80° C.)
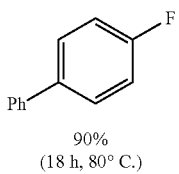
90%
(18 h, 80° C.)
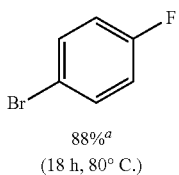
88%[a]
(18 h, 80° C.)
TABLE 2-continued
Fluorination of Compounds
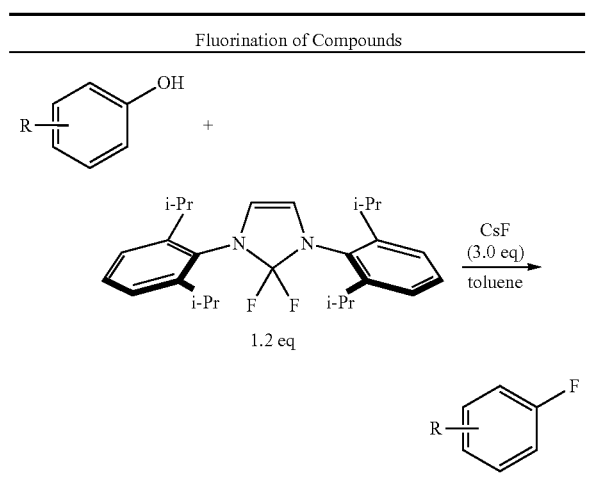
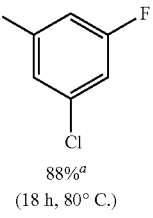
88%[a]
(18 h, 80° C.)
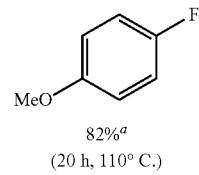
82%[a]
(20 h, 110° C.)
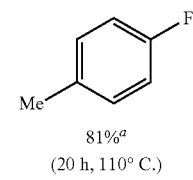
81%[a]
(20 h, 110° C.)
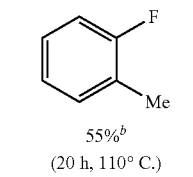
55%[b]
(20 h, 110° C.)
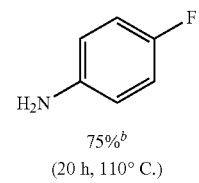
75%[b]
(20 h, 110° C.)
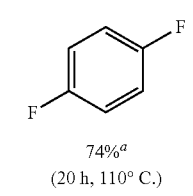
74%[a]
(20 h, 110° C.)

TABLE 2-continued

Fluorination of Compounds

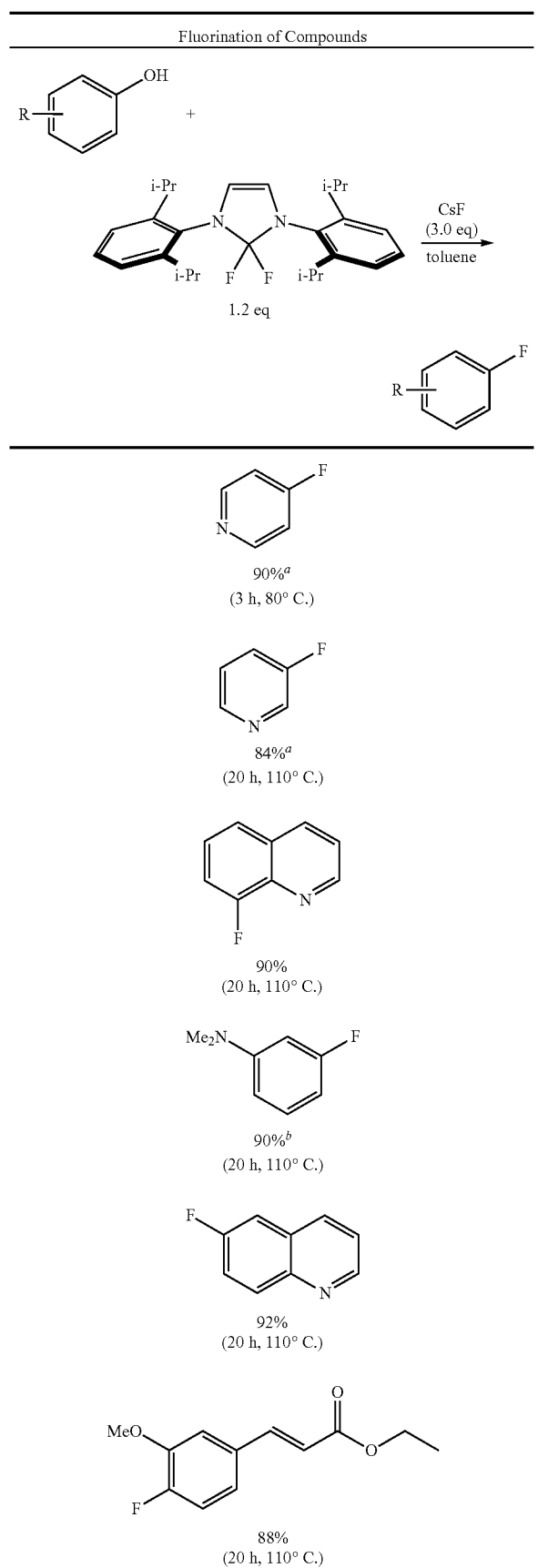

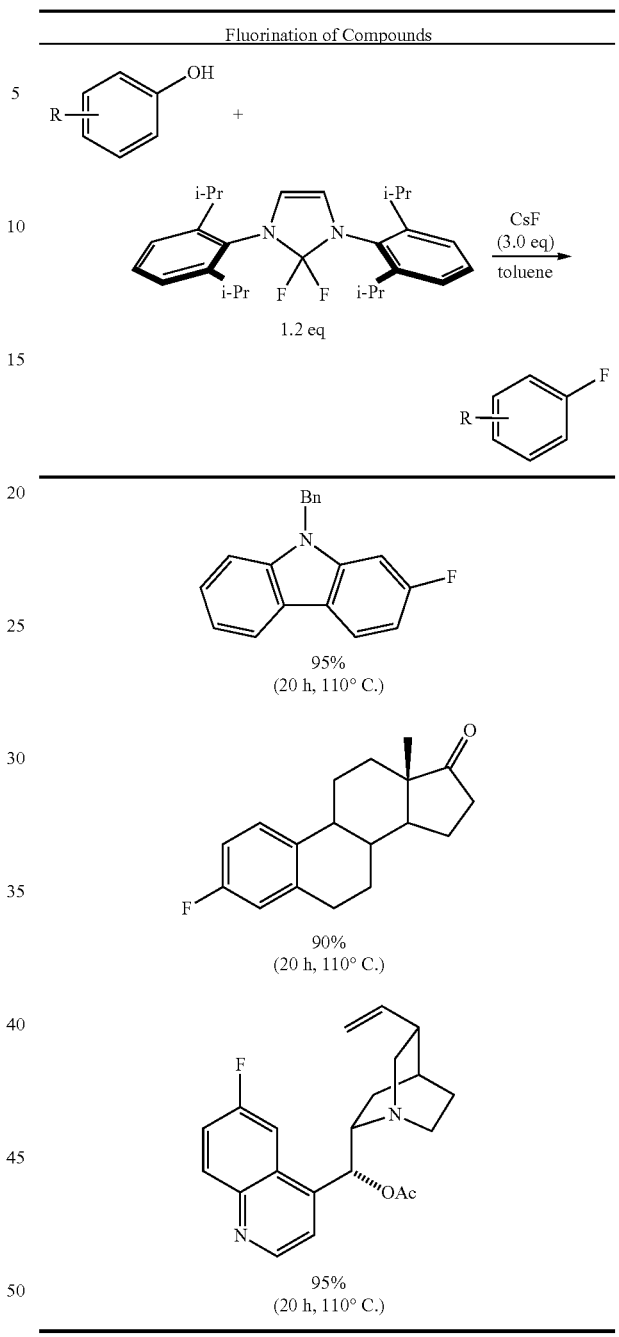

[a] Yields were determined by ¹⁹F NMR with 1-fluoro-3-nitrobenzene as a standard.
[b] 1,4-dioxane was used.

Example 4

General Procedure for Fluorination Reaction with New Fluorination Compound B To phenol (0.020 mmol, 1.0 equiv) in toluene (0.35 mL) at 23° C. was added CsF (6.1 mg, 0.040 mmol, 2.0 equiv), diphenylzinc (0.88 mg, 0.0080 mmol, 0.20 equiv) and N,N'-1,3-bis(2,6-diisopropylphenyl)-2,2-difluoroimidazolidene (B) (10.5 mg, 0.0240 mmol, 1.20 equiv). The reaction mixture was stirred at 80° C. for 20 h in a sealed vial, then cooled to 23° C. To the reaction mixture was added 3-nitrofluorobenzene (2.00 µL, 0.0188 mmol). The yield was determined by comparing the integration of the $^{19}$F NMR (375 MHz, acetone-$d_6$, 23° C.) resonance of 3-nitrofluorobenzene (−112.0 ppm). Yields are reported in Table 2.
TABLE 3
Fluorination of Compounds
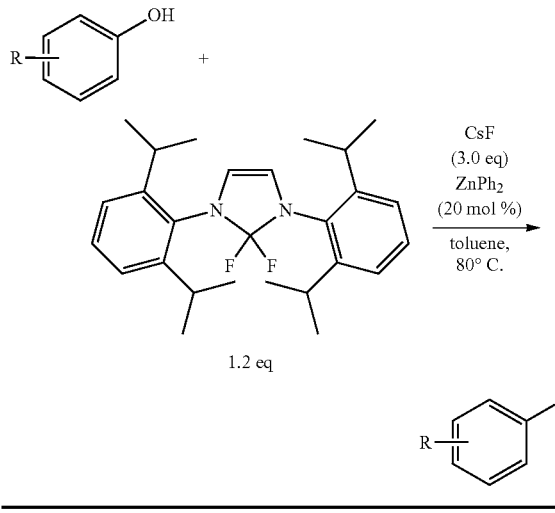
1.2 eq
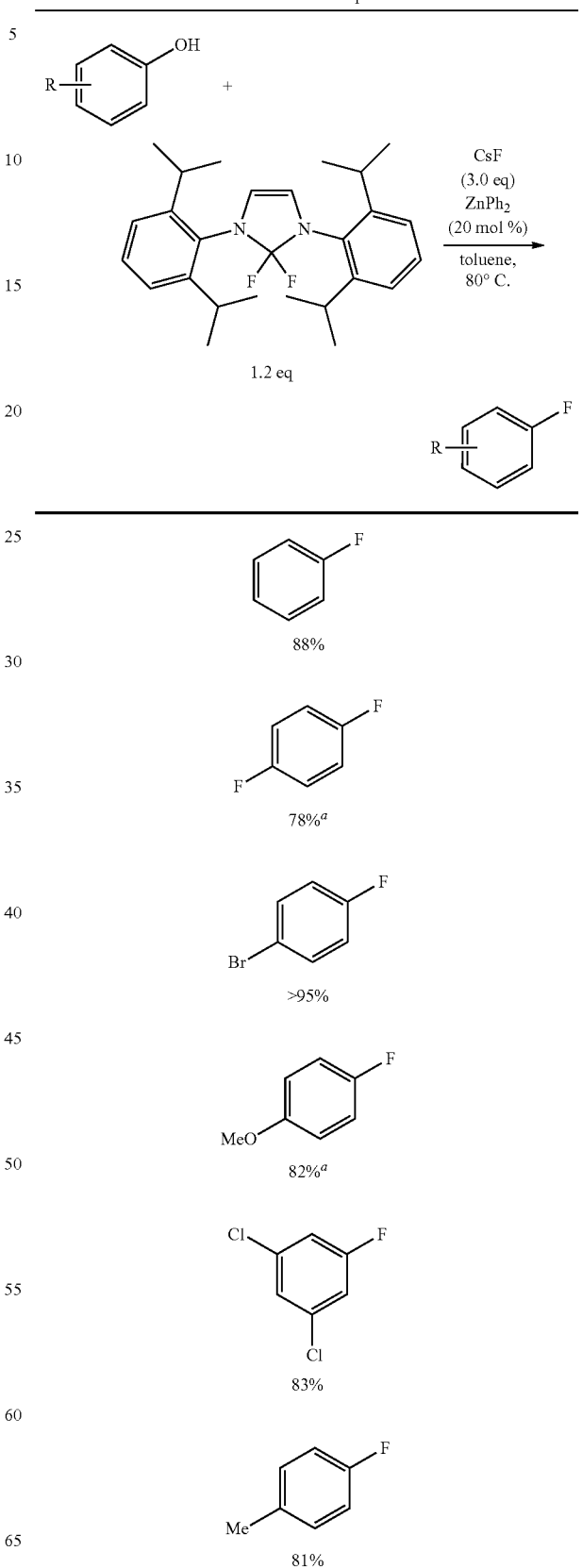

TABLE 3-continued
Fluorination of Compounds
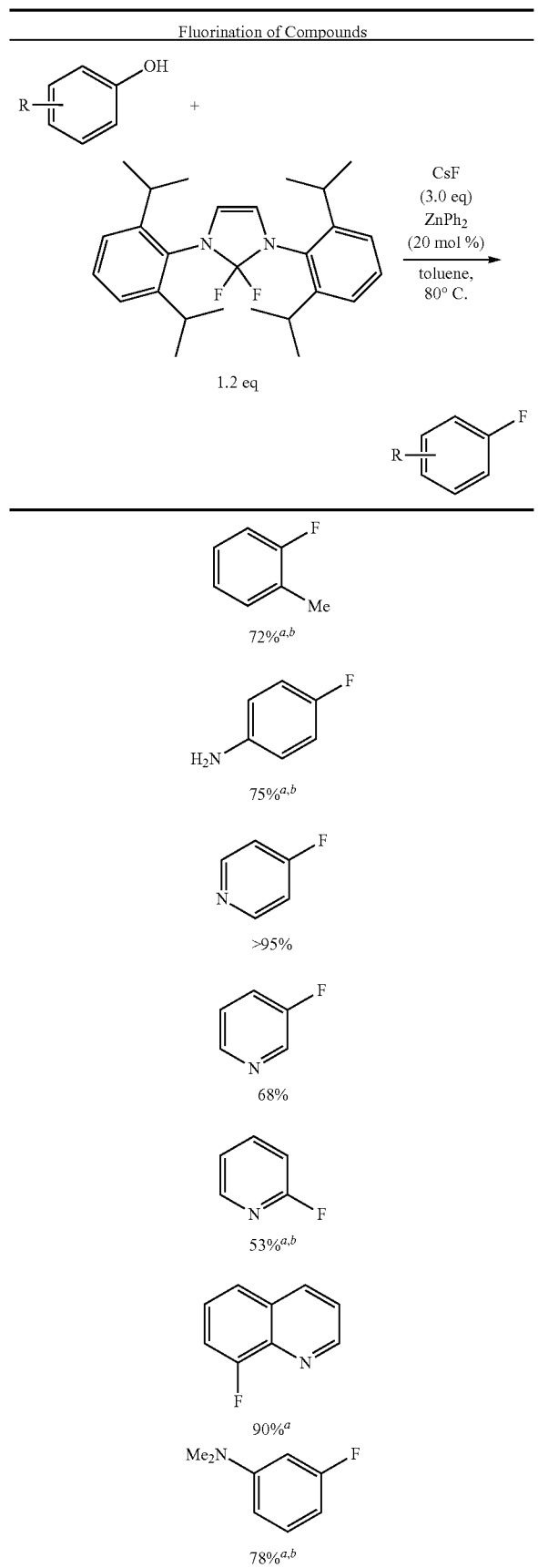
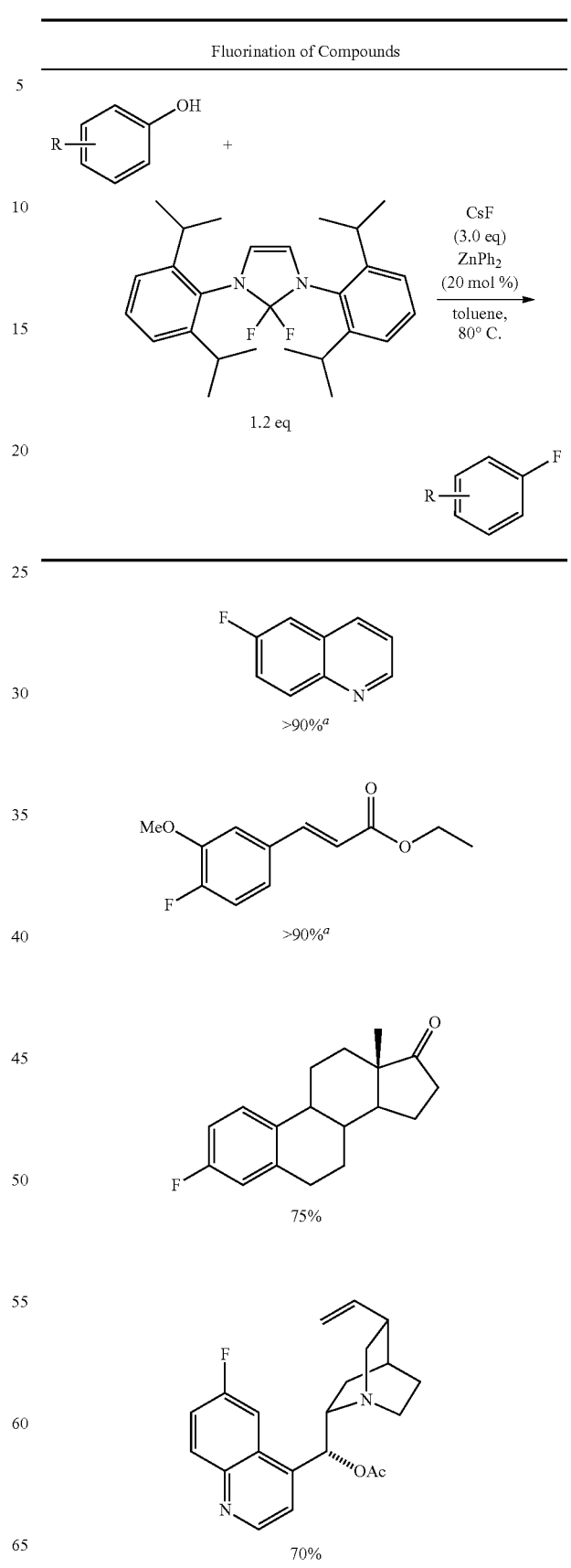

TABLE 3-continued

Fluorination of Compounds

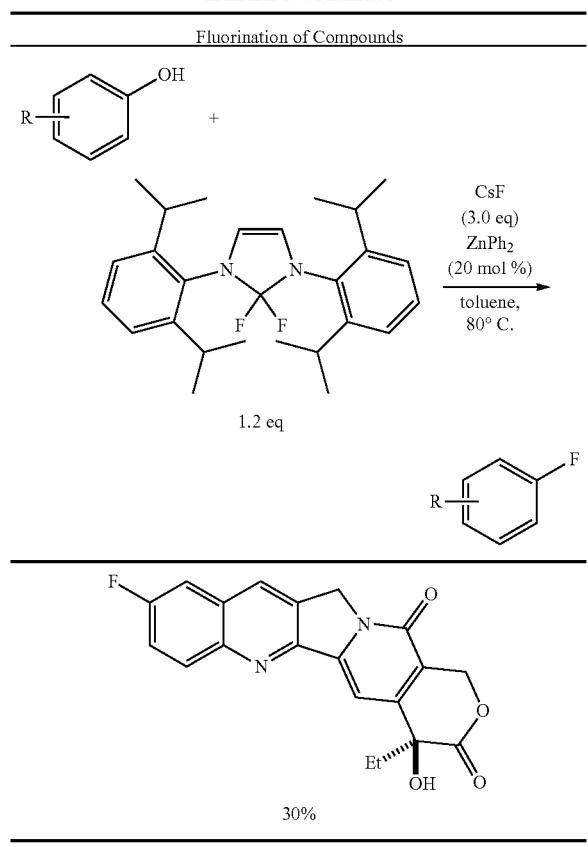

$^a$110° C. was used.
$^b$1,4-dioxane was used.

Example 5

Example for the Fluorination Reaction

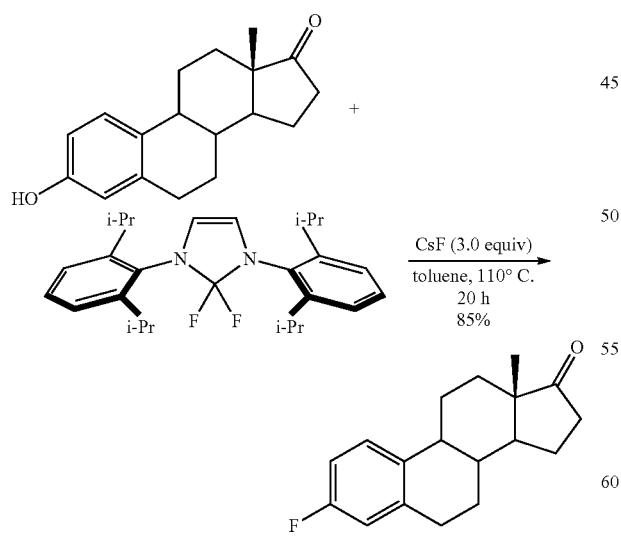

To estrone (106 mg, 0.393 mmol, 1.00 equiv) in toluene (4.0 mL) at 23° C. was added CsF (180 mg, 1.18 mmol, 3.00 equiv) and N,N'-1,3-bis(2,6-diisopropylphenyl)-2,2-difluoroimidazolidene (B) (201 mg, 0.472 mmol, 1.20 equiv). The reaction mixture was stirred at 110° C. for 20 h in a sealed vial, then cooled to 23° C. The reaction mixture was filtered through a pad of celite, eluting with $CH_2Cl_2$ and the filtrate was concentrated in vacuo. The residue was purified by chromatography on silica gel, eluting with Hexane/EtOAc 10:1 (v/v), to afford 90.8 mg colorless solid (85% yield).

$R_f$=0.33 (hexane/EtOAc 9:1 (v/v)). NMR Spectroscopy: $^1$H NMR (500 MHz, $CDCl_3$, 23° C., δ): 7.23 (dd, J=8.0 Hz, 6.0 Hz, 1H), 6.85-6.77 (m, 2H), 2.92-2.88 (m, 2H), 2.51 (dd, J=19.0 Hz, 9.0 Hz, 1H), 2.42-2.38 (m, 1H), 2.29-2.23 (m, 1H), 2.18-1.94 (m, 4H), 1.67-1.41 (m, 6H), 0.91 (s, 3H). $^{13}$C NMR (125 MHz, $CDCl_3$, 23° C., δ): 220.7, 160.9 (d, J=242 Hz), 138.7 (d, J=7.3 Hz), 135.3, 126.8 (d, J=7.3 Hz), 115.1 (d, J=20 Hz), 112.5 (d, J=20 Hz), 50.4, 47.9, 43.9, 38.1, 35.8, 31.5, 29.5, 26.3, 25.9, 21.6, 13.8. $^{19}$F NMR (375 MHz, $CDCl_3$, 23° C., δ): -118.5.

What is claimed is:

1. A compound of formula (I):

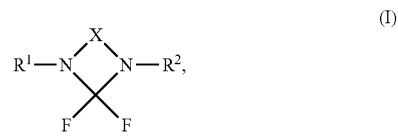

wherein $R^1$ and $R^2$ are each independently selected from $C_{6-12}$ aryl, $C_{6-12}$ aralkyl, 6-12 membered heteroaryl, 6-12 membered heteroaralkyl, 6-12 membered heterocyclyl and 6-12 membered heterocyclylalkyl, each of which is substituted with 0-3 occurrences of $R^5$;

X is an optionally substituted $C_2$-$C_5$ alkenylene moiety each $R^5$ is independently selected from halo, $C_{1-8}$ alkyl, $C_{1-8}$ haloalkyl, $C_{1-8}$ alkoxy, $C_{6-12}$ aryl and 6-12 membered heteroaryl.

2. The compound of claim 1, wherein $R^1$ and $R^2$ are each independently selected from $C_{6-12}$ aryl, 6-12 membered heteroaryl and 6-12 membered heterocyclyl.

3. The compound of claim 1, wherein X is an optionally substituted $C_2$ alkenylene.

4. The compound of claim 1, wherein the compound of formula (I) is a compound of formula (Ia):

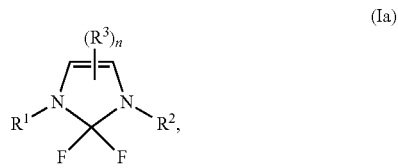

wherein each $R^3$ is independently selected from $C_{1-8}$ alkyl, nitro, cyano, halo, $C_{1-8}$ haloalkyl, $C_{1-8}$ alkoxy, $C_{6-12}$ aryl, $C_{6-12}$ aralkyl, 6-12 membered heteroaryl, 6-12 membered heterocyclyl and 6-12 membered heterocyclylalkyl; and n is 0, 1 or 2.

5. The compound of claim 1, wherein the compound of formula (I) is a compound of formula (Ib):

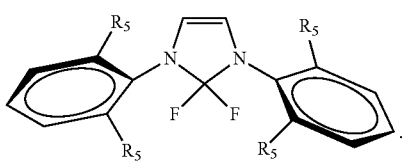

6. The compound of claim 1, wherein each $R^5$ is independently selected from $C_{1-8}$ alkyl, $C_{1-8}$ haloalkyl and $C_{1-8}$ alkoxy.

7. The compound of claim 1, wherein the compound of formula (I) is a compound of formula (Ic):

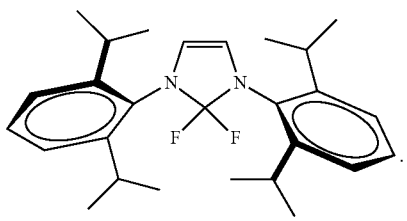

8. A method of producing a compound of claim 1, the method comprising reacting a compound of formula (II):

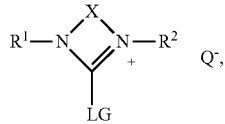

wherein $R^1$, $R^2$ and X are as defined in claim 1; wherein LG is a leaving group; and
Q is an anion;
with a fluorine source to produce the compound of formula (I).

9. The method of claim 8, wherein $R^1$ and $R^2$ are each independently selected from $C_{6-12}$ aryl, 6-12 membered heteroaryl and 6-12 membered heterocyclyl.

10. The method of claim 8, wherein X is an optionally substituted $C_2$ alkenylene.

11. The method of claim 8, wherein each $R^5$ is independently selected from $C_{1-8}$ alkyl, $C_{1-8}$ haloalkyl and $C_{1-8}$ alkoxy.

12. The method of claim 8, wherein the fluorine source is $F^-$ or a salt thereof.

13. A reaction mixture comprising a compound of claim 1, an organic compound and a fluorine source.

14. A composition comprising a compound of formula (I) and an additional component

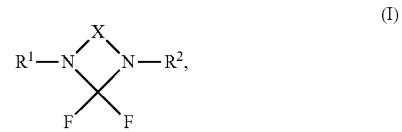

wherein
$R^1$ and $R^2$ are each independently selected from $C_{6-12}$ aryl, $C_{6-12}$ aralkyl, 6-12 membered heteroaryl, 6-12 membered heteroaralkyl, 6-12 membered heterocyclyl and 6-12 membered heterocyclylalkyl, each of which is substituted with 0-3 occurrences of $R^5$;
each $R^5$ is independently selected from halo, $C_{1-8}$ alkyl, $C_{1-8}$ haloalkyl, $C_{1-8}$ alkoxy, $C_{6-12}$ aryl and 6-12 membered heteroaryl;
X is an optionally substituted $C_2$-$C_5$ alkenylene moiety.

* * * * *

UNITED STATES PATENT AND TRADEMARK OFFICE
CERTIFICATE OF CORRECTION

PATENT NO. : 9,150,516 B2
APPLICATION NO. : 13/444676
DATED : October 6, 2015
INVENTOR(S) : Ritter et al.

Page 1 of 1

It is certified that error appears in the above-identified patent and that said Letters Patent is hereby corrected as shown below:

*In the Claims*

Claim 1, column 28, line 37:

"$C_2$-$C_5$ alkenylene moiety;" should be changed to --$C_2$-$C_5$ alkenylene moiety; and--

Signed and Sealed this
Fourteenth Day of June, 2016

Michelle K. Lee
*Director of the United States Patent and Trademark Office*